(12) United States Patent
Gallager

(10) Patent No.: US 10,337,997 B2
(45) Date of Patent: Jul. 2, 2019

(54) SYSTEM FOR RAPID ASSESSMENT OF WATER QUALITY AND HARMFUL ALGAL BLOOM TOXINS

(71) Applicants: Woods Hole Oceanographic Institution, Woods Hole, MA (US); Scott M. Gallager, Woods Hole, MA (US)

(72) Inventor: Scott M. Gallager, Woods Hole, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 15/747,812

(22) PCT Filed: Oct. 14, 2016

(86) PCT No.: PCT/US2016/057006
§ 371 (c)(1),
(2) Date: Jan. 26, 2018

(87) PCT Pub. No.: WO2017/066544
PCT Pub. Date: Apr. 20, 2017

(65) Prior Publication Data
US 2018/0217067 A1    Aug. 2, 2018

Related U.S. Application Data

(60) Provisional application No. 62/241,835, filed on Oct. 15, 2015.

(51) Int. Cl.
*G01J 3/44* (2006.01)
*G01N 21/65* (2006.01)
(Continued)

(52) U.S. Cl.
CPC ............ *G01N 21/65* (2013.01); *G01J 3/0294* (2013.01); *G01J 3/44* (2013.01); *G01N 21/8507* (2013.01);
(Continued)

(58) Field of Classification Search
CPC ........ G01N 21/65; G01N 21/64; G01N 21/85; G01N 33/18; G01J 3/02; G01J 3/44
See application file for complete search history.

(56) References Cited

U.S. PATENT DOCUMENTS 5,581,085 A    12/1996    Reffner et al.
6,727,498 B2    4/2004    Fries et al.
(Continued)

OTHER PUBLICATIONS

Using Nanotechnology to Combat Sea Muck. ScienceLearn Hub. Mar. 19, 2009; Retrieved from the Internet: <http://sciencelearn.org.nz/News-Events/Latest-News/News-Archive/2009-News-archive/Using-nanotechnology-to-combat-sea-much> entire document.
(Continued)

*Primary Examiner* — Abdullahi Nur
(74) *Attorney, Agent, or Firm* — Kean Miller LLP; Robert Devin Ricci; Russel O. Primeaux

(57) ABSTRACT

The present invention is directed toward the early detection of harmful algal blooms. The system employs the ability of whole cell non-contact micro Raman spectroscopy to detect cell pigmentation in such a way that distinct patterns or fingerprints can be assembled. Light field microscopy will provide a fundamentally innovative increase in image and sample volume. Furthermore, darkfield microscopy is employed to capture high-resolution, color images of the detected plankton to increase the accuracy of species identification and classification. Together, this new instrument will provide a powerful yet elegantly simple solution to detection of HAB cells and characterization of environmental conditions.

25 Claims, 11 Drawing Sheets

(51) Int. Cl.
  *G01N 33/18* (2006.01)
  *G01N 21/85* (2006.01)
  *G01J 3/02* (2006.01)
  *G01J 3/10* (2006.01)

(52) U.S. Cl.
  CPC ......... *G01N 33/18* (2013.01); *G01N 33/1826* (2013.01); *G01J 2003/102* (2013.01); *G01J 2003/104* (2013.01); *G01N 2201/0218* (2013.01); *G01N 2201/0221* (2013.01)

(56) References Cited

U.S. PATENT DOCUMENTS

| | | |
|---|---|---|
| 7,657,127 B2 | 2/2010 | Lolacono et al. |
| 8,625,195 B2 | 1/2014 | Lin et al. |
| 8,767,205 B2 | 7/2014 | Johnsen |
| 8,946,660 B2 | 2/2015 | Pelletier et al. |
| 2007/0182959 A1 | 8/2007 | Maier et al. |
| 2010/0168586 A1 | 7/2010 | Hillman et al. |
| 2012/0050520 A1 | 3/2012 | Thoren et al. |

OTHER PUBLICATIONS

Grossmann, Gallager, Mitarai "Continuous monitoring of near bottom mesoplankton communities in the East China Sea during a series of typhoons" J Oceanogr. 71:115-124 (2015).

Carpenter et al "Polystyrene Spherules in Coastal Waters" Science 178:749-750 (1972).

Lechner et al "The Danube so colorful: A potpourri of plastic litter outnumbers fish larvae in Europe's second largest river" Environmental Pollution 188: 177-181 (2014).

| Linear Discriminant Analysis | | | | | | | | | False Positives |
|---|---|---|---|---|---|---|---|---|---|
|  | Af | Am | At | Cs | Cm | Gb | Gc | Kb |  |
| Af | 62.5 |  |  |  |  | 18.8 | 12.5 | 6.3 | 37.5 |
| Am |  | 100 |  |  |  |  |  |  | 0 |
| At |  |  | 93.8 |  |  |  | 6.3 |  | 6.2 |
| Cs |  |  | 6.3 | 87.5 |  |  |  | 6.3 | 12.5 |
| Cm |  |  |  |  | 100 |  |  |  | 0 |
| Gb | 12.5 |  |  |  |  | 75 | 12.5 |  | 25 |
| Gc |  |  |  |  |  |  | 100 |  | 0 |
| Kb |  |  | 6.3 | 6.3 |  |  |  | 87.5 | 12.5 |
|  |  |  |  |  |  |  |  |  | 88.2875 |

FIG. 10

SYSTEM FOR RAPID ASSESSMENT OF WATER QUALITY AND HARMFUL ALGAL BLOOM TOXINS

CROSS REFERENCE TO RELATED APPLICATIONS

This application is the National Stage of International Application No. PCT/US2016/57006, filed Oct. 14, 2016, which claims the benefit of U.S. Patent Application Ser. No. 62/241,835, filed Oct. 15, 2015. Furthermore, the entire contents of the U.S. Pat. No. 7,415,136 entitled "Optical Method and System for Rapid Identification of Multiple Refractive Index Materials Using Multiscale Texture and Color Invariants," the PCT Patent Application No. PCT/US15/51121, entitled "Continuous Particle Imaging and Classification System," and publication Mitarai et al. (2015) "Continuous monitoring of near-bottom mesoplankton communities in East China Sea during a series of typhoons" J Oceanogr. 71:115-124 are incorporated herein by reference and without disclaimer.

FIELD OF THE INVENTION

The present invention generally relates to the fields of optical imaging and spectroscopy. More specifically, this invention is related to the techniques for detecting, observing, imaging, calculating concentration, and/or classifying the species and/or strains of plankton, particularly algae involved with harmful algal blooms, and microplastics.

BACKGROUND OF THE INVENTION

Harmful algal blooms (HABs) exert strongly negative impacts on coastal oceans, lakes, rivers, and municipal drinking supplies world-wide. These can be seen, for example, either directly though production and release of potent neurotoxins and/or through massive die-offs that induce anoxic conditions and extensive fish-kills. Contamination of shellfish with toxins produced by HABs continues to be an ongoing concern for the fisheries, aquaculture industry, and research fields as the HABs cause ocean closures, sale bans, and consumption restrictions. Not only are HABs harmful for human consumers, but the toxic blooms are often devastating to the ecosystem and to a large variety of marine organisms. HABs can have a direct, potentially fatal, effect on humans.

Consumption of shellfish contaminated with algal toxins can cause paralytic shellfish poisoning (PSP) which can be potentially fatal. Several types of toxins associated with HABs have been characterized including saxitoxin, neosaxitoxin, gonyautoxin, decarbamoyl saxitoxin, among others, particularly produced by plankton belonging to the genera *Alexandrium, Gymnodinium, Pyrodinium*, and *Pseudo-nitzschia*.

Remarkably, there remains no simple, straightforward, precise, rapid, and low-cost technique to identify the diverse array of HAB cells and their toxins from water samples. As such, the ability to characterize the plankton community at the species level provides an immensely valuable index of ecosystem condition and how it may be changing relative to climate change and ocean acidification. Identification of plankton on the spatial and temporal scales necessary to use diversity and abundance as an environmental index is a very difficult problem and goes well beyond technicians with plankton nets or filtering devices and laboratory microscopes and high-performance liquid chromatography (HPLC) and liquid chromatography-mass spectrometry (LC-MS) analytical instrumentation. A truly useful plankton index of environmental health and water quality requires real-time, automated approaches to species identification and quantification of potential toxins on temporal/spatial scales of seconds and meters. Such instruments must provide precise and accurate answers quickly and be sufficiently inexpensive to be available on every swimming beaches and in every municipal reservoir in the country. Instruments need to be in the water, sampling continuously, and sending their processed data products to managers and scientists world-wide without delay. Additionally, they must be robust to corrosion, biofouling, and mechanical damage. Such systems need be sufficiently intelligent to understand and separate background noise from a true signal, and capable to parse and integrate a variety of information from a variety of sources.

Therefore, there exists a need for new systems and methods for accurately identifying species and strains of algae pertaining to HABs on a real-time and accurate basis.

DESCRIPTION OF THE DRAWINGS

Other features and advantages of the present invention, as well as the invention itself, can be more fully understood from the following description of the various embodiments, when read together with the accompanying drawings, in which:

FIG. 10 depicts a table of the accuracies of the Leave-One-Out Cross Validation analysis.

DEFINITIONS

Figure 1A:
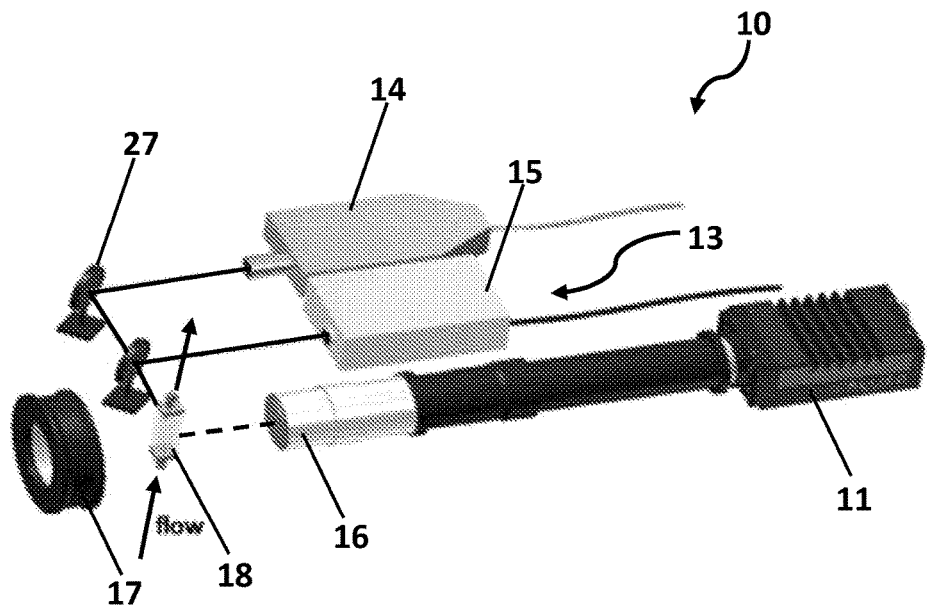
FIG. 1A depicts a perspective view of the flow-through and passage of light in the system. Shown in diagrammatically FIG. 1B, the camera and telecentric lens view the flow-through space illuminated by a strobed LED ring illumination system. Following extraction of the target Region of Interest (ROI), the laser is directed and pulsed at a point set to excite the same target but displaced just slightly in the target space based on flow speed through the cell.

Continuous Particle Imaging and Classification System. As used herein, this expression or "CPICS" refers to the system as referenced from PCT/US15/51121.

Target. The object of interest present in the surrounding (e.g., aquatic, marine) environment capable of being imaged by the CPICS. The space surrounding the "target" may be referred to as a "region of interest" or "ROI". In many embodiments, the target is a marine organism, in particular a plankton, microorganism, or particle present in environment. The primary requirement of the target is that it is capable of passing though the target space for imaging by the optical system and is detectable by the optical system. In many embodiments, it is intended, although not required, for the target to be of a size suitable for imaging within the target space, typically in the size range of at least 1 µm, up to 10 µm, and up to about 10 cm.

Harmful Algal Bloom. A harmful algal bloom or "HAB" is considered one or more colonies of plankton which comprise one or more toxic compounds which include plankton of the class of dinophagellates, cyanobacteria, haptophytes, raphidophytes, and diatoms as well as any other plankton comprising a toxic compound of interest.

Platform. The platform is the vehicle or structure on which the continuous particle imaging device is mounted. The platform may be stationary or mobile, and may comprise a such as a structure like an underwater observatory node, a mooring, a buoy, a drifting buoy, a float, a CTD rosette (conductivity/temperature/depth sensor), a tripod, a mount, a bench, a counter, a vehicle like an autonomous underwater vehicle (AUV), an unmanned remotely operated vehicle (ROV), a human occupied vehicle (HOV), a glider, a kayak (e.g., Jet Yak), a submarine, a mini submarine, or towed body towable by a vehicle, vessel, diver, or other suitable means.

Optical System. The optical system provides the means to manipulate the light path and properties thereof and to facilitate the imaging and/or spectrum acquisition of the target of interest. The system is capable of producing high-resolution images of targets in motion and/or stationary when said targets are disposed within the target space. In general, the optical system comprises a darkfield optical assembly further comprising a camera, a lens (e.g., a telecentric lens), a housing (e.g., water-tight, pressure-resistant), and a Raman spectroscopic assembly further comprising a spectrometer, a laser, and a beam splitter. Additionally, other components include those necessary to process the images and/or spectrum of targets including an image processor and a computer. In many embodiments, the particle imaging device employs a high-resolution optical system wherein the optical system is capable of imaging fine features of a target often as small as 1 µm at an image quality suitable for image processing and classification by the disclosed methods.

Camera. The optical system comprises a camera capable of high-resolution (e.g., high quality) imaging of targets potentially in motion. Although any suitable camera may be employed with the present invention, some preferred embodiments include a camera adapted to operate in an aquatic environment with various environmental conditions and produce images of targets at a quality suitable for accurate classification.

Lens. The lens is a transparent substance or material capable of receiving certain light beams (the secondary light beams) and directing and/or focusing the light beams in a manner to allow the components of the optical system to receive and manipulate said light beams to produce an image or data. In many embodiments, the lens is a telecentric lens wherein only scattered and diffracted light, which is being redirected by a target that comes between the primary light source and the lens within the target space, enters the lens. Zero order light, or light that does not intersect any target, is directed to infinity. In normal operation, a target present within the target space will reflect, deflect, or refract light emanating from the primary light source, to produce secondary light rays which impinge on the distal lens surface (the image face) of lens, such that the optical system (i.e., the camera) may generate images of the target.

Target Space. In general, the target space is defined as the space capable of accommodating a target for imaging or detecting, often as a substantially open, free-flow (e.g., multi-directional flow) space, wherein targets present in the surrounding environment typically may enter, be introduced, move through without deterrence and, in most embodiments, without force such as from pumping, and are imaged by the optical system. While the target space may be open to allow targets to enter and exit from any side, the target space may be limited to a portion of open space in the target space, the primary light beams produced from the primary light source intersect/converge and may impinge a target disposed in this space to produce secondary light beams (e.g., light scattering) which are received by the lens to generate an image.

Path Length. As used herein, the term refers to the overall distance between the primary light source (the light array) and the optical system the image face of the lens. In some embodiments, the connection means defines the path length, positioning the primary light source a distance from the optical system. In many cases, the path length may be adjusted to provide a distinctness or clarity of an image rendered by an optical system imaging of targets within the target space.

Focal Distance. The focal distance, also "focal range" or focal volume" refers to the overall length between the distal face of the lens and its point of focus. At the point of focus, a target may produce secondary light beams to impinge the image face of the lens and provide an in-focus image of the target.

Primary Light Source. The primary light source, also "light source", provides the means of illumination for the optical system to produce images of targets wherein the primary light source is comprised of one or more suitable light-emitting sources capable of producing light beams to impinge a target in the target region to produce secondary light beams. More specifically, the preferred primary light source is adapted to produce a suitable amount of secondary light beams through an aquatic environment for imaging a target. The positioning of primary light source is constrained that in normal use in the absence of a target within the focal range or target space of the lens, the preponderance of light beams from the primary light source does not impinge on the distal face of the lens.

Structure. In many embodiments, the light source is mounted on the structure or appropriate mounting surface to secure the light-emitting sources of primary light source at the appropriate orientations to illuminate targets in the target space. The light source and structure may be collectively referred to as the light array or depending on the embodiment, the LED array and are generally located beyond the focal distance of the lens. In many embodiments, the structure allows the light-emitting sources to be positioned at one or more angles directed toward the central imaging axis in order to produce primary light beams which do not impinge the distal face of the lens.

Housing. Referred to herein as the "housing" or "camera housing", this component fits or otherwise securely mounts the optical system and associated components within the internal space of the housing. In many embodiments, the housing is intended to protect the optical system and to withstand the pressure forces exerted by the surrounding environment which may vary depending upon the depth of desired deployment of the inventive particle imaging device. In many cases, the housing is designed to resist degradation from external forces such as water, salt, dust, and other environmental and circumstantial conditions. The housing is typically connected to the primary light source via the connection means wherein a space (e.g., target space) is disposed between the primary light source and the housing.

Anti-Fouling System. A means to reduce, prevent, clean, and/or remove the build-up of microscopic and macroscopic organisms, referred to as bio-fouling, from a surface(s) exposed to the surrounding environment such as the primary light source, the distal face of the lens, or any specified surface of the present invention.

Connection Means. The means to mount, secure, or otherwise orient the primary light source (e.g., light array) at the suitable distance and orientation from the optical system. The connection means is designed to not detrimentally affect the required rate of fluid movement through the target space and at a minimum will connect at one point to the optical system or its housing and at one point to a primary light source (e.g., the light array) in such a way as to not interfere with illumination of the target space, or the optical pathway necessary for image production.

Central Imaging Axis. This axis may be defined by an imaginary line passing through the center of the lens and propagated through the device.

Primary Light Beams. The primary light source is configured in a suitable orientation to emit primary light beams (e.g., primary light rays) of a desired wavelength(s) to emanate into the focal volume and intersect (e.g., converge) on a target. In most embodiments, the primary light rays intersect within the target space but do not impinge on the distal face of the lens.

Secondary Light Beams. Secondary light beams (e.g., secondary light rays) are generally characterized as the redirected light beams generated when the primary light beams are reflected, deflected, refracted, or altered in their projected path by a target. The secondary light beams may then impinge the distal face of the lens and contribute to the imaging of said target by the camera of the optical system.

Storage Device. The storage device provides the means for storing the raw, processed, altered, etc. images and necessary forms of data acquired or programmed in the continuous particle imaging device. Any suitable means for storing said data may be employed including a hard drive(s), a solid state drive(s), or similar system as deemed fit by one skilled in the art. Said storage device may by connected (e.g., in communication) with the image processor or on-board computer and/or another location. In most embodiments, the storage device is capable of transmitting the stored images and/or data to another location such as a vessel, vehicle, land-based facility, buoy, mooring, server, website via a wired (e.g., fiber optic, high-speed, Ethernet) or a wireless (e.g., satellite) connection. In some embodiments, the storage device also stores metadata (e.g., position, orientation, depth, time, crystalline material, transparency, etc.) related to each imaged target (e.g., ROI).

Ethernet Interface. As used herein, the Ethernet interface refers to the connectivity with the optical system. Typical Ethernet connection speeds range from 2 megabits per second to 10 gigabits or more. The Ethernet interface may be directly incorporated with the continuous particle imaging device or provided through an external source including, but not limited to, a towed vehicle, a CTD rosette, a cabled observatory, or a mooring. In several embodiments, the Ethernet interface can be controlled from a vessel or from shore through custom software and a configuration file that contains the operating information.

SUMMARY OF THE INVENTION

The present invention relates to systems and methods for characterizing aquatic environments and the presence of algal toxins, particularly those produced during an algal bloom, and other targets of interest including microplastics.

One embodiment of the inventive system includes a lab bench prototype light field microscope capable of detecting the presence of a target, specially a target associated with harmful algal blooms, and producing a Raman spectrum of the target. Another embodiment depicts includes a lab bench prototype light field microscope further comprising a dark-field optical assembly wherein the system is capable of detecting the presence of a target, producing a Raman spectrum of the target, and capturing a high-resolution image of the target. Furthermore, each of the above embodiments of the inventive system may be adapted to be submerged in an aquatic environment to detect the presence of a target, to produce a Raman spectrum of the target, and/or capture a high-resolution image of the target in situ.

DETAILED DESCRIPTION OF THE ILLUSTRATED EMBODIMENTS

The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

Furthermore, the described features, structures, or characteristics may be combined in any suitable manner in one or more embodiments. In the following description, numerous specific details are provided, such as examples of cameras, mirrors, sensing information, and components. One skilled in the relevant art will recognize, however, that the system for rapid assessment of water quality and harmful algal bloom toxins, sometimes referred to as the HAB detection system for ease of reference, may be practiced without one or more of the specific details, or with other methods, components, materials, and so forth. In other instances, well-known structures, materials, or operations are not shown or described in detail to avoid obscuring aspects of the invention. Other components and apparatuses may be conceived that are equivalent in function, logic, or effect to one or more mechanisms, or portions thereof, of the System.

The invention may be better understood through the following detailed description describing various embodiments to a system adapted to repeatedly transport a sensor suite vertically through the water column to acquire high vertical and high temporal resolution observations of various aspects and parameters of the sampled body of water.

The invention may be better understood through the following detailed description describing various embodiments to a novel system adapted for the identification of plankton, specifically those involved in HABs, using in situ light field (LF) microscopy coupled with Raman spectroscopy to provide distinct species-species fingerprints. Light field microscopy offers a fundamentally progressive increase in sample volume, further providing a powerful yet simple solution to the detection of HAB cells. In one or more embodiments, the disclosed method includes a fingerprinting feature for the characterization of organic composition, type (e.g., species, strain), and concentration of HAB neurotoxins. Such a method can be employed using the economical, robust instrument package adapted to withstand the conditions of the aquatic environment.

The ability to detect the presence and concentration of HAB cells and their toxins in unprocessed water, cells, and/or tissues using Raman spectroscopy allows for rapid, inexpensive, on-location screening (e.g., beaches, shellfish farms, aquaculture sites, point-of-sale transactions) saving millions of dollars and potentially human lives.

The physics of aquatic environments fundamentally limits sampling ability to two energy modalities: sound and light. Acoustics have often been used to characterize communities of fish and plankton and the seafloor from great distances, but the spatial resolution is fundamentally limited by wavelength to targets larger than about 1 cm. Light on the other hand can be used to resolve targets as small as bacteria cells, but attenuation is frequency dependent, and the propagation limited to meters. Nevertheless, light is generally the mode of choice when discrete small particles such as imaging individual plankton since it is possible to resolve the setae on the antennules of copepods and the flagella of toxic dinoflagellates.

As depicted, the inventive system, referred to herein as the HAB detection systems generally comprises a sensor package which includes the aspects of: 1) imaging, classifying, and quantifying microplankton (10 µm-200 µm), mesoplankton (500 µm-2 cm), and in some embodiments, macroplankton (2 cm-20 cm) to produce high resolution, color imagery with defined precise sampling volumes; 2) employing optical engineering to maximize image volume by imaging in three-dimensions; and 3) incorporating Raman spectroscopy to provide a specific fingerprint of the sample.

As color, structure, and size information is critical to species identification, a high resolution imaging device is essential to capture precise details characterizing each species. One suitable device referred to as the Continuous Particle Imaging and Classification System (CPICS), filed in the PCT Patent Application PCT/US15/51121, enables the collection of such information. CPICS uses darkfield illumination provided by a proprietary LED array synchronized with the frame rate of a high resolution machine vision color camera. The imaged volume is unobstructed and open to the free-flow stream fluid, allowing very delicate cells (e.g., *Acantharia*, HAB cells), organisms (e.g., salps, dolilids, *Trichodesmium* sp.), and aggregates (e.g., marine snow) to be imaged non-invasively at high resolution, characterizing and quantifying critical color information that represents chlorophyll, beta-carotene, and other important high molecular weight pigments.

The invention describes a plankton and particle in situ microscopic imaging system that produces crisp light field images and an integrated micro Raman spectrometer that captures the fingerprint of the imaged target. The system and methods are appropriate for imaging and categorizing ultrafine materials having a similar color, shape, texture, morphology, and features that are difficult to identify through conventional imaging methods due to a lack of distinguishing characteristics of the imaged target. Such features include structures which may be transparent, opaque, delicate (e.g., about 1 µm), and crystalline, among other aspects which are difficult for adequately capturing high quality images and providing high accuracy classification.

Particular advantages of the present invention include providing a small particle imaging device often capable of being hand-held for allowing easy transportation. The device usually allows open flow through the target imaging space which permits the imaging of plankton and particles in their natural orientation, in undisturbed predator-prey interactions, and without damage. The present invention uses a novel optical system capable of providing high-resolution color information which is a particularly key aspect to increasing the accuracy of plankton identification. Additionally, the imaging device is easy to operate, automatically quantifying the individual organisms and populations of the imaged targets and performing Raman spectroscopy of the targets. The resulting data may be easily analyzed to provide a unique Raman spectrum of each target used to determine the presence of species of plankton involved with HABs.

Turning to the Figures, an illustrative embodiment of the CPICS is shown. The high-resolution machine vision camera 11 depicted in FIG. 1 operates at a variety of frame rates limited only by the speed of the connection of the camera to the image processor. The high-resolution machine vision camera 11 is coupled with an advanced lens system 16 such as a telecentric lens and a structured lighting system 17 which may comprise a known light array, such as a LED array for illumination purposes. The camera 11 also generally incorporates the use of an Ethernet interface with the image processor to allow connectivity using high speed communications to transmit the images and data to another location, although such connection may be remote through a telemarking device such as or not at all.

Figure 1B:
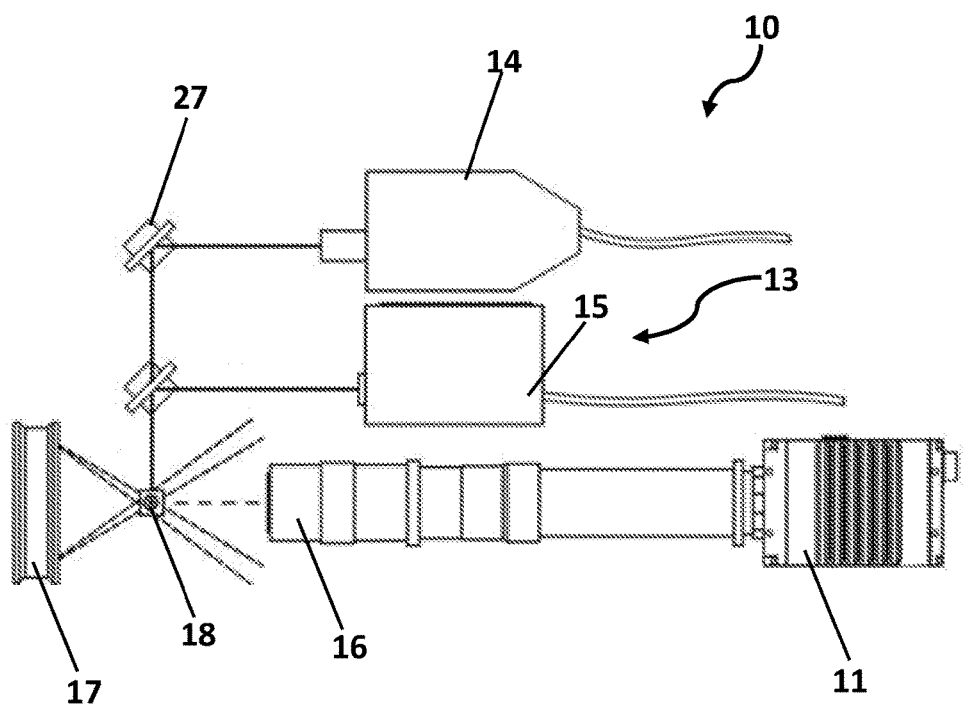
FIG. 1 is one illustrated embodiment of a flow-through Continuous Particle Imaging and Classification System (CPICS) HAB system.

The use of a telecentric lens 16, which is contained in the housing 12, schematically depicted in FIGS. 1A and 1B, is designed to produce maximal depth of field (DOF), at the same magnification throughout the entire space of the focal distance (e.g., focal volume). This allows the targets to be measured much more accurately than with a traditional lens. The telecentricity also removes any barrel distortion at the corner of the image that would disturb normal lenses and decrease reliability of image classification.

A precise volume sample is obtained by imaging at rates faster than the flow rate of the fluid past the sensor (e.g., 6 Hz) and then tracking targets through multiple images thereby providing multiple images of the same target in different orientations as well as defining the rate at which new samples are taken. In some embodiments, the color images are transmitted via Gigabit Ethernet on a fiber optic cable along with their metadata, which may be in the form of raw data to a computer where targets such as cells or whole organisms are detected by advanced machine vision software and the Region of Interest (ROI) surrounding the target is extracted and saved.

Simultaneously, a process selects the ROI and extracts a variety of features (e.g., texture, color, and shape being most important) and runs the feature sets through a statistical classifier such as Support Vector Machine or Random Forest (RF) that has been trained by expert plankton taxonomists. The featured extraction process is further described in U.S. Pat. No. 7,415,136. Depending on number of classes and distinctiveness of the targets, accuracies approaching 80%, 85%, 90%, 95%, and over may be obtained. While all of this processing and classification is currently completed on a computer independent to the imaging sensor, this technology may be embedded within the instrument itself thereby providing data products directly from the instrument. The present invention described here is a modified system of the CPICS capable of detecting targets of interest, particularly harmful algal bloom cells or microplastics, which provides an expanded sample volume by using light field imaging and organic characterization at the molecular level using micro Raman spectroscopy.

As previously discussed, HABs are a worldwide phenomenon and occur in just about every known coastal and inland region. HABs significantly impact public health, fisheries, tourism, and the functioning of whole ecosystems. As such, research programs have been developed in every major country in an attempt to understand where, how and why HABs form and why they persist. While progress has been made in many research areas, such as in the isolation, characterization, and synthesis of many neurotoxins, there still remains no simple, straight forward, precise, rapid, and low cost technique to identify HAB cells and their toxins.

HABs come in a variety of conditions and produce either distinct toxins or no toxin at all. In the latter case just the abundant biomass that is produced causes extensive hypoxic and anoxic conditions leading to fish kills, among other environmentally damaging issues. In addition to high biomass, non-toxic HABs such as *Aureococcus anophageffer-ens* can also interfere with suspension feeding in shellfish and attached to the gills of fish reducing gas exchange efficiency.

HABs may be clustered into three primary categories (see Example 2). Most of these dinoflagellate cells are between 20 and 40 Lm in diameter and can be effectively imaged using a 10×-20× magnification microscope objective. Some are quite large such as *Noctiluca scintillans* (about 1 mm or greater in diameter) and, these cells can be imaged on the CPICS. Structurally, the toxins of eukaryotic microalgae can be classified into several major groups, the most prominent groups comprising: 1) linear and macrocyclic polyethers (e.g., okadaic acid, dinophysistoxins); 2) ladder-frame polyethers (e.g., brevetoxins, ciguatoxins); 3) macrocyclic imines (e.g., spirolides, gymnodimine); 4) tetrahydropurines, (e.g., saxitoxin and analogs); and 5) toxic secondary amines, including domoic acid.

Traditional analytical approaches to detect and quantify these toxins in shellfish and directly in the environment include Gas Chromatography (GC), High Pressure Liquid Chromatography (HPLC) and GC Mass spectroscopy (GCMS). These lab-based analytical techniques are sensitive, typically to pg/cell, and highly discriminatorily able to resolve several different forms of toxins in a mixture. One particularly toxic and ubiquitous HAB species in the Gulf of Mexico region is *Karenia brevis* and its co-occurring and toxic congeners. This species produces a pigment called gyroxanthin-diester which has been used as a biomarker of the species. However, not all HAB species contain distinct pigment signatures such as *Karenia brevis* so identification must be largely through analytical means. The toxicity of HAB cells is highly variable from species to species and apparently under environmental control as a function of nutrient limitation (e.g., nitrogen, nitrate, phosphorus, phosphate). For example, *K. brevis* produces potent neurotoxins (e.g., brevetoxins) at concentrations from 1-68 pg/cell, with such variation a function of phosphate limitation rather than nitrate.

Instrumentation that can be deployed in the field to monitor the physics of such events have been around for decades, but biological sensors that can detect and classify phytoplankton and zooplankton are just beginning to catch up. As noted above, most of these instruments are in their early research phase and will probably require several more years before commercialization and wide availability to scientists and managers.

Light Field Microscopy

Three dimensional microscopic imaging through reconstruction of light fields provides an immense increase in the sample volume (e.g., FOV) thereby enabling identification of micro plankton (plankton about 10 to 200 μm) and particularly toxic dinoflagellates at relatively low concentrations without the need for injection into a traditional flow cell. However, while light field microscopy is well-known and characterized on the lab bench, it has not been carried out in an aquatic environment.

Unlike conventional microscopy where the focal length (FL) and depth of field (DOF) are established a priori in the optical design, a microscope that captures the entire light field permits manipulation of the DOF and focus after the image is necessary for accurate species classification. While diffraction at sub-micron scales limits the product of spatial and angular resolution in light field imaging, complete and continuous three-dimensional (3D) focal stacks and 3D volumes may be produced using standard deconvolution algorithms at 1 μm resolution. In addition, improvements in optical design in light field microscopy have led to the use of wavefront coding to provide an even distribution of spatial-resolution regardless of DOF. For example, with a 16×0.4NA objective using light field microscopy with wavefront encoding, the DOF may be enlarged from a typical 3.34 μm to 1 mm, a factor of 300 times the normal DOF. This means that organisms or particles of diameter 20 μm (e.g., dinoflagellate) and diameter 500 μm (e.g., copepod nauplii) may be imaged in 3D entirety in a single image at spatial resolution (e.g., height-width-depth).

Figure 2:
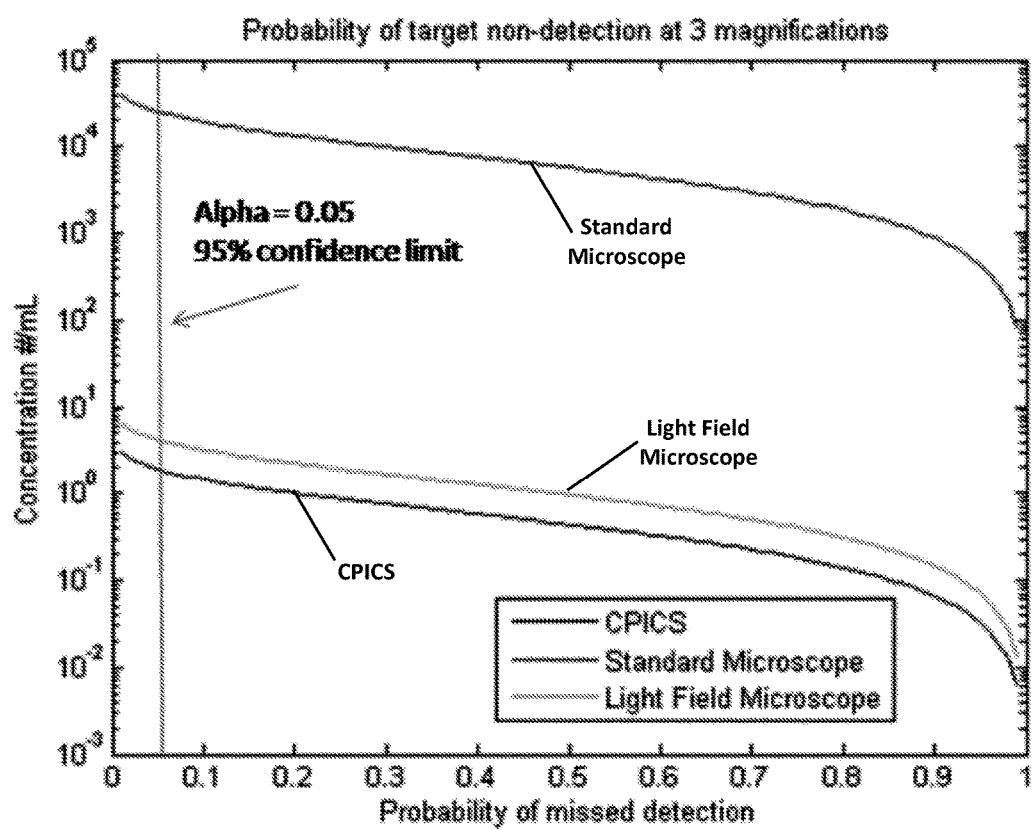
FIG. 2 depicts a graph of the probability of non-detection of HAB cells as a function of cell concentration using three imaging systems. Because the target space volume of the light field microscope is 300× that of the standard microscope, it can detect and quantify cell concentration under natural field conditions which is not possible using a standard objective lens.

The probability of non-detection of HAB cells may be defined as a function of cell concentration using three imaging systems (FIG. 2). Because the sample volume of the light field microscope is 300× that of the standard microscope, cell concentration can be detected and quantified under natural field conditions which is not possible using standard objective lens resolution of approximately 1 μm. Additionally, given the ability to reconstruct a 3D volume in its entirety through deconvolution, the effective sample volume is enlarged by at least a factor of 300, making the quantification of small organisms and particles at low concentrations a reality. Maximizing the image volume to detect HAB blooms in the field is critical for detecting precise details of ROIs and properly classifying the species. The image volume and hence the sample volume dictates how often it is expected to observe a target given a specific target density or concentration. For example, the concentration of HAB cells under non-bloom conditions can be very low, just a few cells per liter (around 0.002 cells/mL). Under bloom conditions, the concentration can increase by many folds to well over 1,000 cells/mL.

In order to determine the accuracy of the detection system, the probability of missing, or not detecting, a cell using imaging systems with certain sample volumes need to be determined. This may be accomplished by simulating a cell population using a Poisson expansion where the probability of non-detection p is: $p(n=0)=e-\lambda v$ where $\lambda$ is the cell concentration in the field in cells/mL and v is the sample volume in mL. By providing the sample volume of three instruments, the equation can be solved for $\lambda$ by the following: $\log(p)=-\lambda v$ and $-\log(p)/v=\lambda$.

At least three embodiments of the imaging systems are envisioned including: 1) a standard microscope with an objective lens (e.g., 10×, 20×, 30×, 40×) where the sample volume is the image width×length×DOF. The image width and length may be fixed at 1 mm and 1 mm, respectively. The DOF in this case is very small (e.g., approximately 0.002 mm); 2) a light field microscope with the same width and height but the DOF is 300× greater than a standard microscope lens giving 0.06 cm; and 3) a standard CPICS system with an image width and length of 12 mm×11 mm and DOF of 2 mm. The probability of non-detection for these three systems as a function of cell concentration is given in FIG. 2. If a probability is set at an alpha of 0.05 (95% confidence limit), the cell concentration must be at least 30,000 cells/mL before the standard microscope lens can be used to accurately detect and quantify cell concentration. This is very high and probably rarely encountered in the field. Using the CPICS intercept at alpha=0.05, the CPICS is capable of quantifying a cell density of 2 cells/mL. However, the CPICS magnification is relatively low, and a 20 µm dinoflagellate would appear as a large blob. Analyzing the curve for the light field microscope, it is observed that good resolution of the cell population is achieved as low as 8 cells/mL, which is a concentration typically found in the field as blooms start to become concentrated. The threshold concentration for an alert to be initiated is typically around 100 cells/mL, however this threshold may be increased or decreased based on the target species of interest. In some embodiments, the alert threshold is set at 10 cells/mL, 20 cells/mL, 40 cells/mL, 60 cells/mL, or 80 cells/mL. In other embodiments, the alert threshold is set higher with 100 cells/mL up to 1,000 cells/mL. The light field microscope achieves the production of a very high resolution image of a HAB cell as though it were on a microscope with a 10× objective, but under natural field concentrations without the need to concentrate or otherwise inject a sample through a flow cell and substantially disturb the cell to cell distances or damage fragile particles and aggregates.

Figure 3:
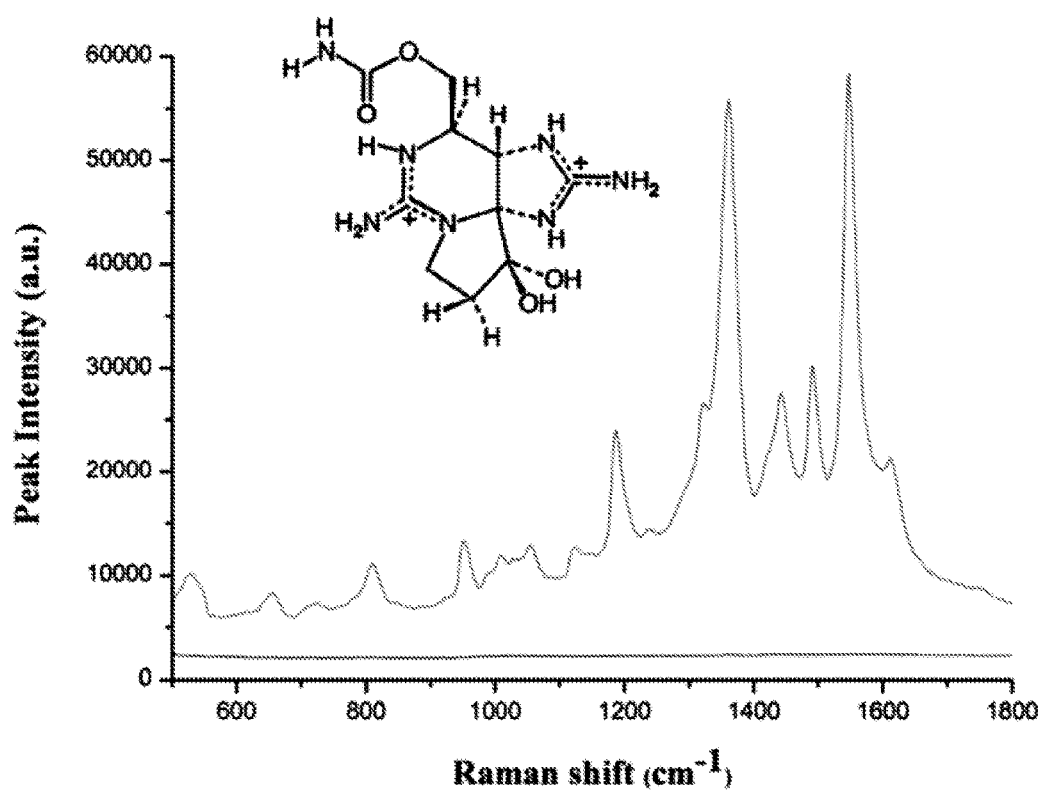
FIG. 3 depicts the chemical structure of saxitoxin (STX) and its related surface-enhanced Raman spectroscopic signature.

To date, there remains no simple, straight forward, precise, rapid, and low-cost technique to identify the diverse array of HAB cells and their toxins from water samples. While the present invention has adapted light field microscopy to capture cell images, Raman spectroscopy is employed to provide a strong and distinct signal or fingerprint of HAB cells and their toxins. Shown in FIG. 3 is an example fingerprint spectrum of the harmful algal bloom toxin saxitoxin. This type of vibrational spectroscopy is based on the non-destructive inelastic Raman scattering of molecular bonds providing identification of solids, liquids, and gases in multiple species simultaneously without the need for regents. Monochromatic laser light is focused on a target in air or water and the wavelength shifted Raman scattered radiation is collected and measured by a spectrometer. Micro Raman Spectroscopy (MRS) is essentially a Raman spectrometer mounted on a microscope to provide high magnification images of targets and precise positioning of the laser. For example, when viewing HAB dinoflagellate cells with a MRS, the operator can pinpoint within 2 µm the area to be measured. This allows cell maps to be created of organic and inorganic composition, particularly the position and concentration of lipids and pigments to be made with relative ease. The intensity of Raman scattering is inversely proportional to the wavelength to the fourth power. In many embodiments, the Raman spectroscopic assembly uses a 532 nm laser, which produces more than 4× more scattering energy than longer wavelengths used commonly in industry, such as 785 nm. The 532 nm green light minimizes fluorescence in phytoplankton cells, a common and difficult to remove interference that can mask the Raman signal. Seawater has a weak Raman signal making it very useful for work in the ocean. In other embodiments, the Raman spectroscopic assembly uses a 632 nm laser or a 1024 nm laser.

HAB Detection System

The inventive HAB detection system comprises many of the aspects of the CPICS with the addition of several key features to provide a plankton and particle in situ microscopic imaging system that utilizes light field microscopy for imaging and Raman spectroscopy for signature fingerprinting. In another embodiment, the system uses dark field microscopy to image the target and Raman spectroscopy for creating a signature spectrum of the target. In another embodiment, the system uses both light field and darkfield microscopy. Using a spectrometer built into the system, referred to herein as the Raman spectroscopic assembly, Raman-scattered radiation is collected and measured by a spectrometer without the need for sample preparation, reagents, a traditional flow cell, or other very expensive laboratory (e.g., analytical) equipment. Turning to FIG. 1 the system generally includes: an optical system 10 contained within a system housing 12 and further comprising a camera 11, a Raman spectroscopic assembly 13 comprising a spectrometer 14 and a laser 15, a lens 16, a light source 17 for illuminating targets 22, a connection means 19 for attaching the light source 17 a distance from the system housing 12 (and optical system 10), and a target space 18 disposed between the system housing 12 and the light source 17.

In operation, the camera 11 takes an image of a target 22 in the target space 18 as the light source 17 is strobed on in synchrony. The raw image passes through the lens 16 immediately in front of the camera 11. The entire light field volume is contained within the raw image. As the darkfield array turns off, the laser fires immediately wherein the spectrometer 14 integrates Raman scattered photons and produces a raw spectrum. The raw image and raw spectrum are saved with identical timestamps to the nearest microsecond and transmitted to the computer via a transmission means such as a fiber optic cable. The computer then locates the target 22 in the image, draws a bounding box (virtually) and extracts the ROI as a deconvoluted light field image.

The present system may be adapted to separate and discriminate between algal species including those causing HABs and between multiple strains of the same species that have originated from different geographic regions. Additionally, the detection system may be capable of detecting algal cells (e.g., HAB cells) at low concentrations. While these lab-based analytical techniques are sensitive, typically to pg/cell, the system is capable of detecting single HAB cells and alerting when concentrations of such cells have reached a threshold defined by the user.

Targets of Interest

The present invention provides a submersible imaging system capable of high-resolution imaging of targets 22 disposed in an aquatic environment (e.g., salt water, fresh water, brackish water, water column, liquid medium). Because many of the targets 22 are very fragile and possess delicate crystalline spines or other fine features, they are typically not well-imaged or disposed in their natural orientation when captured in an enclosed chamber or other collection means. A particular feature of the present invention is the free-flowing open space, the target space 18, wherein the targets 22 are imaged without damage (e.g., without contact, without collection), allowing high quality imaging of even the most delicate and fragile species, such as the *Acantharia*.

The target space 18 may be limited to a defined flow-through area. In many embodiments, the target space 18 is disposed between the light source 17 and the optical system 10. In a specific embodiment, the target space 18 is defined to a 1 cm$^2$ section wherein water and material present in the water may pass through. At an area of 1 cm$^2$, the flow-through velocity is anticipated to be approximately 160 mm/s or 0.16 µm/µs and with a light source strobe rate of 10 µs, an image of a target in this window will be smeared across the CCD chip for a distance of 1.6 µm, which equates to approximately ¼ of a pixel. At 10 frames per second (fps), nearly the entire volume of 1 L/min will be imaged, and the sample volume can be calculated. In other embodiments, the target space 18 is of a defined flow-through area greater than 1 cm$^2$ and is matched with flow-through-through velocity speed, light source strobe rate, and imaging rate. In other embodiments, the target space 18 is less than 1 cm$^2$.

The system is capable of imaging numerous targets. Such targets include, but are not limited to, microorganisms such as algae, diatoms, plankton (e.g., phytoplankton, holoplankton, meroplankton, zooplankton), Coccolithophores, pteropods, dinoflagellates, *Acantharia*, Echinoderm larvae, Foraminifera, radiolaria, larvae (e.g., invertebrate larvae animals), bacteria (e.g., cyanobacteria, *Trichodesmium*), protozoa (e.g., coral, Bryozoa, rotifers, sponges, polchaete worms), jellyfish (e.g., hydromedusae, gelatinous organisms, osmoconformers), ctenophores, tunicates (e.g., salp), small crustaceans (e.g., copepods, Brachiopods, Remipedia, Cephalocarida, Maxillopoda, Ostracoda, Malacostraca), Chaetognatha, fishes, larval fishes, particles (e.g., dissolved organic material, inanimate fragments, marine snow, microscopic materials, detritus, dead particulates, biomass), or any suitably sized microorganism or particle.

Targets of particularly interest associated with harmful algal blooms include, but are not limited to: *Gonyaulux polygramma*, *Noctiluca scintillans*, *Scrippsiella trochoidea*, *Aureococcus anophagefferens*, *Cochlodinium polykrikoides*, *Karenia mikimotori*, *Chattonella antiuqua*, *Chattonella marina*, *Alexandrium catenella*, *Alexandrium fundyense*, *Alexandrium minutum*, *Alexandrium tamarense*, *Gymnodinium catenatum*, *Psedo-nitzschia australis*, *Psedo-nitzschia multiseries*, *Pseudo-nitzschia seriata*, *Gambierdiscus polynesiensis*, *Karenia brevis*, and all species described in Example 2. Additional targets of interest may include one or more plankton comprising a compound of interest wherein the compound of interest is defined a known set of signature Raman spectroscopic peaks.

Other uses of the present system include the identification of targets comprised of plastic such as microplastics commonly found dispersed in the water column as described in Example 3.

In general, any target (e.g., ROI, organism, or particle) disposed within the open space of the imaging region, specifically the target space 18, may be imaged by the present invention. Such targets include those of a size less than 1 µm, 5 µm, 10 µm, 1 µm to 10 µm, 10 µm to 50 µm, 10 µm to 100 µm, 10 µm to 200 µm, at least 100 µm, at least 500 µm, at least 1 mm, up to 5 mm, up to 10 mm, 10 µm to 10 mm, up to 100 mm, up to 1 cm, up to 5 cm, 1 µm to 10 cm or more. Features of the target 22 are fine as 1 µm (and in some cases, less than 1 µm) may be imaged by the device.

The light source 17 provides the necessary illumination for the system. In most embodiments, a light source 17 is mounted on a structure, collectively referred to as the light array 17, which is attached to the optical system 10 by a connection means 19. The structure 23 of the light source 17 is generally located beyond the focal distance of the lens 16. In normal operation, target 22 within the target space 18 will reflect, deflect, refract, or direct light emanating from the light source 17, causing redirected "secondary" light beams 21 to impinge on the distal surface (e.g., image face) of lens 16, such that the camera 11 may generate images of the target 22 (FIG. 6).

Figure 6:
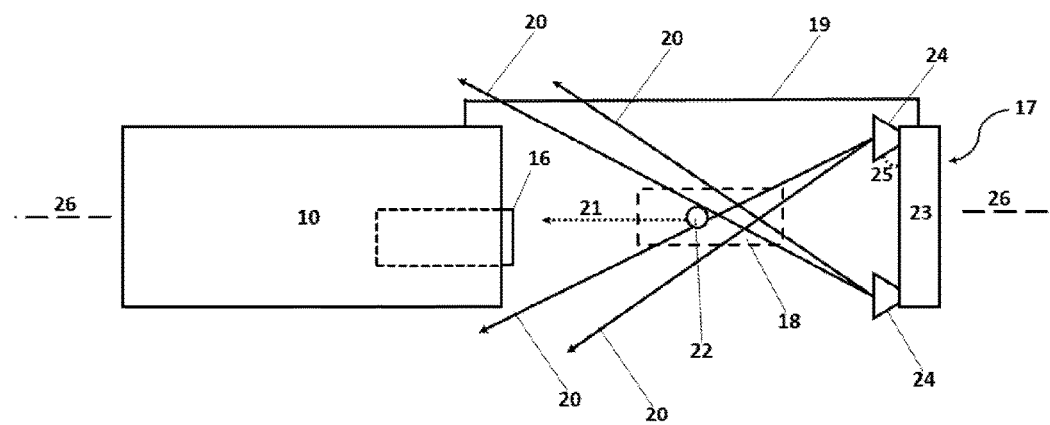
FIG. 6 is a block diagram of one embodiment of the system. The lines demonstrates how the light-emitting sources are positioned to direct light rays at an angle that does not directly enter the camera lens but instead produced a structured light field. The structured light field intersects and illuminates only within the target space in the view of the camera lens.

Depicted in FIG. 6, the light source 17 is comprised of one or more light-emitting sources capable of generating primary light beams 20 to impinge a target 22 in the target space 18 to produce one or more secondary light beams 21. More specifically, the preferred light source 17 is adapted to produce primary light beams 20 through an aquatic environment. In one embodiment, the light source 17 is selected to produce a suitable amount of light for imaging (e.g., observing, classifying, identifying) a target 22 in its surrounding environment with relatively little to no disturbance to the surrounding environment.

In some embodiments, the light source 17 generates monochromatic (e.g., single wavelength or single color light), polychromatic (e.g., 2 or more wavelength light or multiple color light), or white light according to the needs of use. Preferred primary source wavelengths include 300 nm to 800 nm, 380 nm to 760 nm, 100 nm to 400 nm (ultraviolet light), 300 nm to 400 nm (blue-green electromagnetic spectrum), 600 nm to 700 nm (red electromagnetic spectrum), 600 nm to 800 nm, visible light, and infrared light, however, any suitable wavelength light may be used to with the light source 17. In some embodiments, red light is employed in the primary light source which is less visible to microorganisms and prevents aggregation of the plankton swarming about the light array 17. This may be a considerable issue in certain environments and may potentially skew imaging and quantitation. In one embodiment, the light source 17 is comprised of one or more red light-emitting sources 24. In further embodiment, the light source 17 is comprised of a combination of one or more red light-emitting sources 24 and one or more white light-emitting sources 24 (or other desired wavelength(s)).

In many embodiments, the light source 17 is comprised of one or more light-emitting diodes (LEDs) but may be any suitable light-emitting sources 24 as known in by one skilled in the art. In one embodiment, the primary light source 17 is an LED array comprised of numerous high output LEDs (e.g., 2 LEDs, 10 LEDs, 20 LEDs, 50 LEDs, 70 LEDs, 100 LEDs, 150 LEDs, 200 LEDs, 250 LEDs, up to 300 LEDs, up to 400 or more LEDs) arranged in a configuration optimal for the particular optical system 10 such that the LED array 17 light output converges in the defined target space 18 in a region between the array 17 and the lens 16. In one aspect of this embodiment, the light from the LED array 17 is monochromatic in the blue spectrum. In other embodiments, the LED array 17 generate red light, white light, or a combination thereof, depending on whether color imaging is desired. It is readily understood that alternate light sources other than LEDs can be used as would be understood by one having skill in the art.

As the lights sources will be used in aquatic environments it is preferable to waterproof the electronics. Each LED may be disposed in a casing for mounting to the structure 23. In some embodiments, the casing is comprised of anodized aluminum. In alternate embodiments, each LED may be secured within their casing using an adhesive such as potting or other suitable sealant to adapt the light sources 17 for the aquatic environment.

The described light source 17 may also be arranged to provide a conservative use of light to avoid deterring organisms away from the target imaging space 18. In one or more embodiments, the light output from the light (e.g., LED) source 17 is strobed in synchrony with or at a specified rate relative to the camera's 11 exposure duration (e.g., in phase with each frame of the camera 11) to provide an image that is free of motion artifacts even when the system is in motion or being towed at high rates of speed. In one embodiment, the strobe provides a pulse length of light of 5 µs. In other embodiments, the strobe pulse length is specified to be approximately 1 µs, 2 µs, 3 µs, 4 µs, 6 µs, 7 µs, 8 µs, 9 µs, 10 µs, or longer depending on the camera's exposure time.

In some instances, the lens 16 will detect light emitted from targets 22 within the target space 18. Examples of such emitted light include natural or induced fluorescence, autofluorescence, or bioluminescence. For the purposes of this description, such emitted light is also considered to be "secondary" light due to its origination from a secondary light source (other than light source). Primary light beams 20 from light source 17 never reach the camera lens 16 (in the absence of a refracting or reflecting object).

The structured light source 17 comprising the array of light-emitting sources 24 may be configured in any useful way. In one embodiment employing LEDs, the light-emitting sources 24 are arranged in a circular configuration in which the diameter of the array (e.g., the structure 23) is approximately the same size or larger than the size of the camera housing 12. In another embodiment, the diameter of the array is smaller than the size of the camera housing 12. In another form, the diameter of the array is smaller or larger than that of the lens 16. Provided the focusing of the LED beams produces an adequate target space 18, non-circular LED array configurations may be used, including elliptical, trapezoidal, parallel piped, triangular, rectangular, etc. In some embodiments, one or more primary light sources 24 are configured lateral to the target space 18.

The structure 23 provides the surface to which the light-emitting sources 24 are mounting and is typically attached to the outer surface of the housing 12 of optical system 10, to the outer face of the lens 16, or any suitable region of the particle imaging device by a connection means 19 (described in more detail below). The structure 23 may be any suitable shape useful for mounting the light-emitting sources 24 particularly at suitable angles 25 to direct the primary light beams 20 to illuminate the target 22 without providing additional light directly to the lens 16. In some embodiments, structure 23 is a circular (e.g., spherical, round) mounting surface; in further aspects of this embodiment, the light-emitting sources 24 are arranged in a circular configuration. In some cases, structure 23 is an annular or ring shape (e.g., illumination ring) with a cylindrically hollow center (e.g., o-ring), the light sources 17 may be arranged about the diameter of the ring. In other cases, structure 23 is a disc shape wherein the light sources 17 may be arranged in any suitable manner about the planar surface of the disc. In other embodiments, the structure 23 is of an elliptical, trapezoidal, parallel piped, triangular, rectangular, horseshoe, semicircular, linear, or parallelogram form.

Structure 23 may be comprised of any suitable material capable of submergence in water and resistant to deformation at least the minimum desired depth of deployment of the particle imaging device. Such materials may include, but are not limited to, steel, stainless steel, thermoplastics, plastics, natural or synthetic polymers (e.g., delrin, polyethylene), or any appropriate material known in the art.

In order to provide proper beam direction, the structure 23 may comprise mirrors or semi-mirrored surfaces to direct the light rays 20 produced by the primary light source 17. In some embodiments, structure 23 comprises one or more mirrors disposed at an angle 25 to direct the light rays 20 wherein the angle 25 is typically less than 50 degrees from the central imaging axis 26, preferably less than 45 degrees, more preferably about 42 degrees, or less than 40 degrees (e.g., 32 degrees). The angle 25 of disposition will obviously be tied to the particular embodiment's configuration and a number of factors to be discussed herein. In further embodiments, the mirror(s) mounted on structure 23 are used to direct (e.g., internally reflect) the primary light beams 20, in particular the ultraviolet light rays, to beam onto the primary light source 17 as a means to prevent bio-fouling on the light source 17. Such angling of the mirrors may be optimal as the traveled path length of the ultraviolet light is minimized through the aquatic environment, meaning that less of the light is being absorbed (e.g., attenuated) and more is directed to hit the primary light source 17.

The beam angles 25 of the primary light source 17 are configured so that the emitted primary light beams 20 intersect the focal volume of the lens 16 but do not enter the camera lens 16 (in the absence of a refracting or reflecting object). This configuration results in the lens 16 receiving generally only secondary light 21 from the interaction of the primary light beams 20 with target 22 within the target space 18. Preferred beam angles 25 of the primary light source 17 relative to the rest of the optical system 10 and the central imaging axis 26 that will lead to the optimal generation of secondary light 21 to be received by the lens 16 depend upon a number of factors. These factors may include: the distance between the distal face of the lens 16 and the primary light source 17, the dimensions and location of the focal volume for the lens 16 being used, and the location of the primary light source 17 relative to the image face of the lens 16.

In preferred embodiments and detailed in FIG. 6, the primary light source 17 will only illuminate those targets 22 in the in-focus volume (i.e., the target space 18) at angles 25 less than 50 degrees, more preferably less than 45 degrees, more preferably 42 degrees, and in some cases less than 40 degrees and about 32 degrees relative to the central imaging axis 26. In another embodiment, the primary light source 17 provides illumination to the target space 18 at more than one angle 25; in some embodiments featuring LEDs, the primary light source 17 is configured with 5, 10, or more than 20 different angles 25. In still another embodiment, the beam angle 25 of one or more of the light-emitting sources 24 of the primary light source 17 is adjustable (e.g., manually, electronically, automatically). In one aspect of this embodiment, the beam angles 25 of the light-emitting sources 24 of the primary light source 17 are programmable and controlled by a microprocessor or computer, located within the camera 11.

As described in more detail below, the primary light source 17 may also comprise an anti-fouling system to prevent the build-up of bio-fouling on the optical surfaces (or any desired surface of the device) including the light source 17, the distal face (e.g., window) of the lens 16, or optical window of the optical system 10. Although any suitable anti-fouling system deemed appropriate by one skilled in the art may be used, preferred anti-fouling systems include utilizing a primary light source 17 comprising one or more ultraviolet light-emitting sources 24, a mechanical defouling device, a lens 16 with anti-fouling properties, and a combination thereof.

In some embodiments, the present invention employs a primary light source 17 comprised of a plurality of light-emitting sources 24, in particular LEDs, wherein a portion of the plurality of LEDs is selected to emit ultraviolet light. In further embodiments, approximately for every 3-4 light-emitting sources 24 used for imaging illumination, an ultraviolet LED is incorporated into the primary light source 17. In another embodiment, at least one-third of the light-emitting sources 24 emit ultraviolet light. In one embodiment, at least one-half of the light-emitting sources 24 emit ultraviolet light. In another embodiment, two-thirds or more of the light-emitting sources 24 emit ultraviolet light.

In some embodiments, the primary light source 17 comprising one or more ultraviolet light-emitting sources 24 provides an anti-fouling capacity using emitted ultraviolet light directed to radiate on select regions of the device including the primary light source 17 and any optical windows of the optical system 10. In cases where the primary light source 17 strobes the light-emitting sources 24 intermittently for imaging in synchrony with the frame-rate of the camera 11, the ultraviolet light-emitting sources 24 may strobe intermittently offset in time from the imaging illumination.

In another embodiment, the primary light source 17 comprises ultraviolet light-emitting sources 24 which radiate a dose (e.g., duty cycle) of ultraviolet light to prevent bio-fouling. The optimal dose of ultraviolet light may be dependent on the specific environment including the types of plankton and/or particles present, the depth of deployment, and the radiation wavelength, among other factors as described in the field and in the U.S. Pat. No. 9,235,048, incorporated by reference in entirety. In some aspects, the ultraviolet wavelength is between 200 nm and 300 nm, preferably between 240 nm and 295 nm, and in some cases 265 nm and 295 nm, 265 nm, 295 nm, and any suitable wavelength or range of wavelengths determined to prevent bio-fouling on the inventive device. The ultraviolet radiation may be emitted for a specific amount of time, at a predetermined time, when bio-fouling is detected on the optical windows or other surfaces such as by use of a bio-fouling sensor, or a combination thereof.

Identifying a completely transparent anti-fouling treatment on windows, mirrors, or other desired surfaces that are required to pass undistorted image information has been known to be elusive. In other instances, the optical windows, such as the lens 16, comprise anti-fouling properties such as a coating of colloidal titanium dioxide ($TiO_2$) nanoparticles suspended in a silicon solution on its optical windows and primary light source 17. In addition, a series of high output ultraviolet light-emitting sources 24 (e.g., LEDs) contained in the primary light source 17 are directed at the optical window (e.g., lens) with a $TiO_2$ coating. The ultraviolet light induces the release of hydrogen peroxide ($H_2O_2$) from the surrounding water and the $TiO_2$ coating, providing a continuously ablating anti-microbial surface. Moreover, the photo-induced superhydrophilicity created on the optical window surface provides a secondary mechanism for release of bio-fouling organisms and particles. Additionally, any anti-fouling coating, paint, resin, or treatment that does not degrade the imaging capacity of the continuous particle imaging device may be used.

In other embodiments, a mechanical defouling system may be employed, including a wiper, a scrubber, or similar means. In some embodiments, a diver may perform a manually cleaning of the bio-fouled surfaces.

In one embodiment, the anti-fouling system is disposed about the optical window of the lens 16. The optical window is modified to include a set of LEDs to mitigate fouling and reduce maintenance of the system. In a further embodiment, a set of numerous high output LEDs direct UV light towards the optical window to illuminate at least a portion of the surface area of the window. For example, in various embodiments, 2, 4, 6, 8, 10, 10-20, or more high-output LEDs (at 0.5 mW, 270 nm) direct UV light toward the optical window for a total of 3 mW, 0.5 mW, 1 mW, 2 mW, 4 mW, or more to illuminate at least 80%, 85%, 90%, 95%, 100% of the surface area of the window. In some embodiments, 100 mJ/cm is used as the dose of UV light to prevent the build-up of biofilm.

Connection Means

The primary light source 17 and structure 23, is connected to the optical system 10 or its housing 12 with a connection means 19. Ideally, the connection means 19 will not detrimentally affect the required rate of fluid movement through the target space 18, whether by passive transmission, active diffusion, or with a pumping means. The connection means 19 at a minimum will connect at one point to the optical system 10 or its housing 12 and at one point to the light source 17, in such a way as to not interfere with illumination of the target space 18, or the optical pathway necessary for image production. Functionally speaking, connecting the camera 11 and the primary light source 17 in this manner allows the water containing marine microorganisms and targets of interest 22 to flow freely between the camera lens 16 and the primary light source 17. Rigid connection means 19 such as rods, meshes, plates, tubes, and the like are preferred comprised of any appropriate material including, but not limited to, steel, stainless steel, steel alloy, aluminum, aluminum alloy, plastic (e.g., thermoplastic, polyethylene), fiber glass, or other firm materials. In some embodiments, one or more connectivity rods are used as the connection means 19. In one embodiment, four rods hold the light source 17 in its proper position away from the camera lens 16. In another embodiment, the camera 11, the lens 16, and the light source 17 are incorporated directly into or onto an underwater vehicle with no other mechanical connectivity required. In a similar embodiment, the camera 11, the lens 16, and the light source 17 are incorporated directly into an underwater observatory (e.g., node) and require no addition connection means 19.

In one or more embodiments, the connection means 19 defines the distance between the primary light source 17 and the optical system 10 (e.g., the lens 16), also referred to as the path length. In general, this distance may be adjusted to fit the components of the optical system 10. In some embodiments, the primary light source 17 is disposed a distance from the optical system 10 including distances of less than 1 cm, about 2 cm, 3 cm, 4 cm, 5 cm, 6 cm, 8 cm, 10 cm, 12 cm, 15 cm, 20 cm, up to 50 cm, up to 100 cm or more.

Optical System

The HAB detection system comprises many of the optical system 10 components of the CPICS including the necessary components for imaging of targets 22 using darkfield microscopy. Additionally, the inventive system includes a micro Raman spectrometer assembly adapted to acquire secondary light beams 21 received from the lens 16 and process the light information into a unique spectroscopic fingerprint of the imaged target 22.

Encompassing both the darkfield optical components and the micro Raman spectrometer assembly, referred to as the Raman spectroscopic assembly 13, is the system housing 12 which protects the internal components from the surrounding environment and secures the internal components for reliable and accurate measurements.

The optical system 10 comprises darkfield optical components and is capable of producing high-definition color images of targets 22 in many embodiments at high speed, and in some embodiments while in motion. In order to accurately determine classification and quantification, it is preferable that the optical system 10 is designed to record each target 22 only once. As previously discussed, the optical system 10 comprises a camera 11, a housing 12, a lens 16, and/or other optical components for manipulating the light path and properties thereof to facilitate the imaging of the target of interest 22 (FIG. 1).

Figure 7:
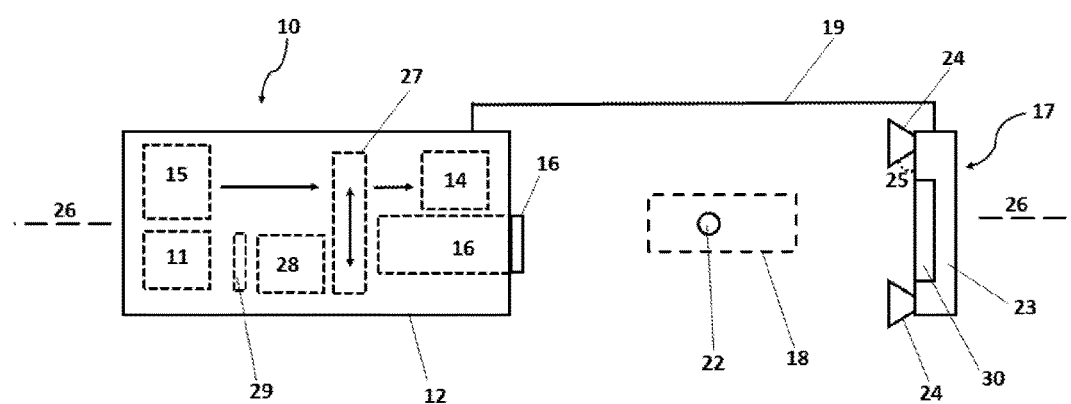
FIG. 7 shows a block diagram of the proposed micro Raman light field microscope. Water flows freely through a target space, allowing unadulterated image samples to be taken. White light in a darkfield arrangement is used to image targets. Simultaneously, a micro Raman spectrometer shoots a laser through coaxial optics at the target and Raman scattered light is received and processed by the spectrometer, according to one illustrated embodiment.

As shown in FIG. 7, the optical components are arranged to define a specific geometry to employ the high-resolution imaging of the continuous particle imaging device dependent upon the telecentric lens 16. Only scattered, diffracted, or redirected light (e.g., secondary light beams 21), which is being passed on by impingement of the plankton and other microorganisms or particles that come between the primary light source 17 (e.g., the LED array) and the camera lens 16, enters the camera lens 16. Zero order light, or light that does not intersect any target 22, is directed to infinity. In many embodiments, the light output from the light source 17 is strobed in synchrony with the camera's 11 exposure duration to provide an image that is free of motion artifacts even when the invention is towed at high rates of speed.

The imaging of targets 22 is facilitated by a suitable camera 11 comprising the capacity to produce high-resolution images of the targets 22 potentially in motion. The camera 11 is generally adapted for operation in a variety of conditions including temperatures ranging from −5° C. to 40° C. (and in alternate embodiments exposure temperatures ranging from −20° C. to 65° C.), pressure from depths down to 6,000 m or more, rough handling, and so forth. In instances where the continuous particle imaging device is mounted on a vehicle or other platform dependent upon battery power, the camera 11 preferably operates at a low power consumption (e.g., less than or approximately 10 W, 8 W, 6 W, 4 W, 3 W, 2 W, 1 W, or less at 12 V depending on the embodiment) to extend the length of time of deployment. Another consideration when deployed on a vehicle or platform is that the camera 11 weight be minimized (e.g., less than or approximately 5 lbs, 3 lbs, 1 lb, 500 g, 400 g, 300 g, 200 g, 100 g, or less).

In many embodiments, the darkfield optical system (and Raman spectroscopic assembly 13) is operably connected to a power source which provides adequate power to operate the electronics of the particle imaging device. The power source may, in some aspects, also be connected to the light source 17. In other embodiments, the light source 17 comprises a separate power source for providing the lighting. The power source may be integrated into the housing 12 of the optical system 10 or disposed externally to the housing 12. In some cases, the power source is provided by the attached platform wherein the particle imaging device is suitably connected to the platform to deliver power for the optical system 10 and/or the light source 17 in addition to any other related components which require power.

In many embodiments, the camera 11 operates at approximately 20 Hz/s (e.g., frames per second, images per second). In other embodiments, this frame rate is up to or approximately 5 Hz/s, 10 Hz/s, 20 Hz/s, 30 Hz/s, 40 Hz/s, 60 Hz/s, 100 Hz/s, 200 Hz/s, or more as deemed appropriate by the user of the particle imaging device. In some embodiments, the camera 11 generated full-frame images at 6 to 10 Hz/s.

The optical window(s) of the optical system 10 may be any suitable material including glass, acrylic, fused silica, or the like as known by those in the art, preferably with minimal interference or distortion of the light (e.g., scattered light) being received from impinging the target 22. The optical window(s) are designed to be a thickness suitable to withstand the pressure or environmental conditions when in operation without failure or infiltration of fluid from the surrounding environment. In some embodiments, the optical window(s) (and the housing 12) are rated to perform to depths at least or approximately 0.5 m, 1 m, 5 m, 10 m, 20 m, 30 m, 50 m, 100 m, 250 m, 500 m, 1,000 m, 2,000 m, 6,000 m, 11,000 m, or full ocean depth.

The frame rate of the camera 11 defines the strobe rate and by carefully selecting the strobe duration, image blurring of moving targets 22 within the target space 18 can be minimized or avoided. Strobing may be programmed to occur as fast as the source lighting 17 and underlying electronics can be made to handle. Strobe duration (e.g., microseconds, milliseconds) is generally controlled by a strobe trigger.

Another factor which generally limits strobe rate is the capacity of the data connection between the camera 11 and the image processing computer (e.g., image processor). Typical connection speeds range from 2-megabits per second to 10-gigabits per second or more. In one embodiment, a 1-gigabit per second connection is used to support frame rates of up to and including 19-frames per second. The use of faster connection speeds enables either or both of more frames per second or increased pixel number or bit depth.

The present invention utilizes a lens or lens assembly 16 with a defined focal length suited to provide high-resolution images with the components of employed optical system 10. As the primary light beams 20 impinge the target 22, secondary light rays 21 are produced and pass through the distal face of the lens 16 before entering the camera 11. The lens 16 is finely positioned and secured through the use of attachment members (e.g., fasteners, screws, bolts, retainers, rings, fixtures) and a suitable lens mount as know by one skilled in the art.

In many embodiments, the system comprises a telecentric lens 16, meaning the magnification of the target 22 (i.e., the image size) is independent of the distance of the camera 11 which allows high-resolution images and accurate size measurements (e.g., diameter, length, profile) of the imaged target 22. Telecentric lenses 16 are also most preferred for their low distortion degree (i.e., the deviation between the imaged and real dimensions of the target 22), which further increases the measurement accuracy and image resolution. Reducing the degree of distortion is especially important for proper target classification as many of the defining features of each target 22 are very fine and are typically indistinguishable by existing imaging devices. Furthermore, telecentric lenses 16 are capable of providing measurements on different target planes, accurately defining the profile of the target, providing even image brightness, and bypassing the need to exactly predict the target-to-lens distance (e.g., focal length). Resulting images of the targets 22 utilizing this lens 16 are captured in amazing clarity.

The use of a telecentric lens 16 provides a large depth of field (microns to centimeters) and a long focal length (i.e., the distance from the focal point of the optical system 10 to the lens 16), facilitating image production with great depths of field relative to particle size. The distal face of the lens 16 (e.g., the end towards the target space 18 through which light enters) is configured in a manner to receive reflected or diffracted light from the particles within the target space 18 (and focal volume). In other embodiments, the system utilizes an infinity corrected objective lens 16.

To modify the CPICS to add Raman spectroscopy (FIGS. 1 and 7), several additional components are integrated, referred to as the Raman spectroscopic assembly 13, which include an optical splitter 27, a laser 15, and a spectrometer 14. As the optical system 10 images targets 22 which pass through the target space 18, the Raman spectroscopic assembly 13 fires the laser 15 through the coaxial optical components at the target 22, and the Raman scattered light is received and processed by the spectrometer 14 to create the target's spectroscopic fingerprint.

Figure 4:
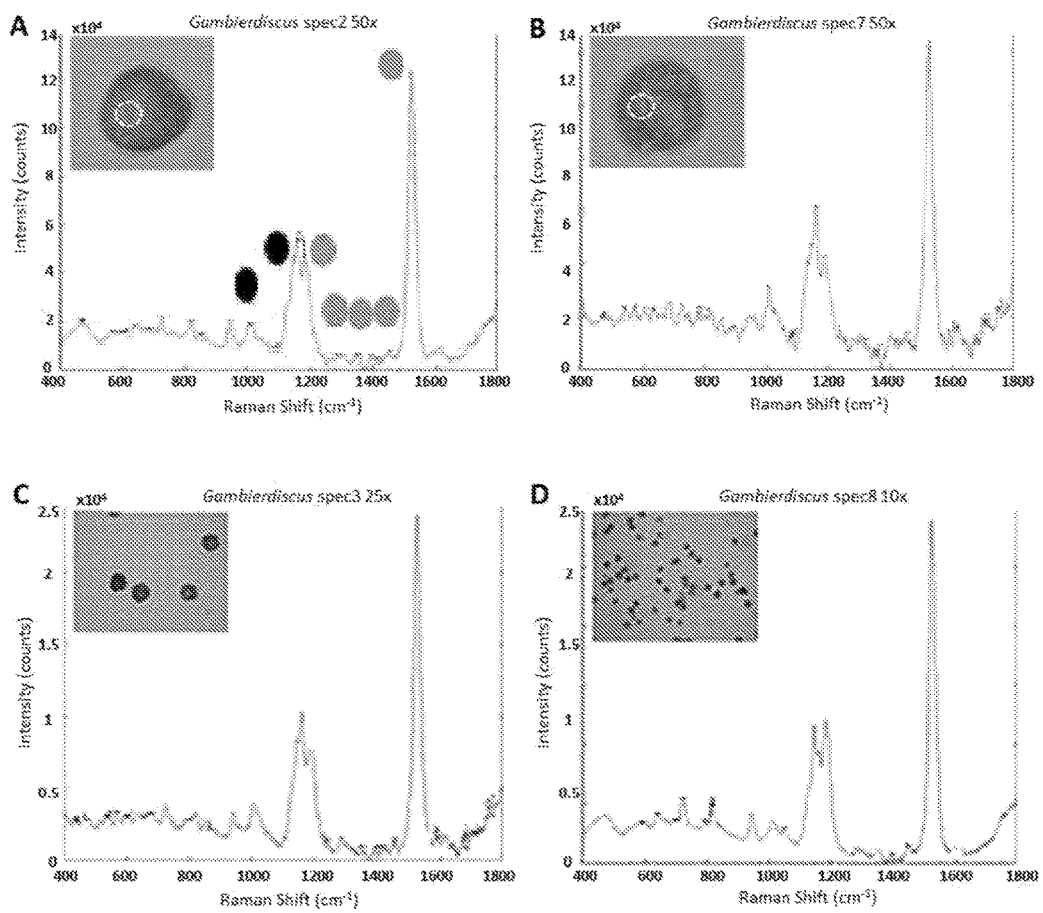
FIG. 4 provides Raman spectra for single cells of *Gambierdiscus silvae* taken at three magnifications 50×, 25×, and 10×.
Figure 5:
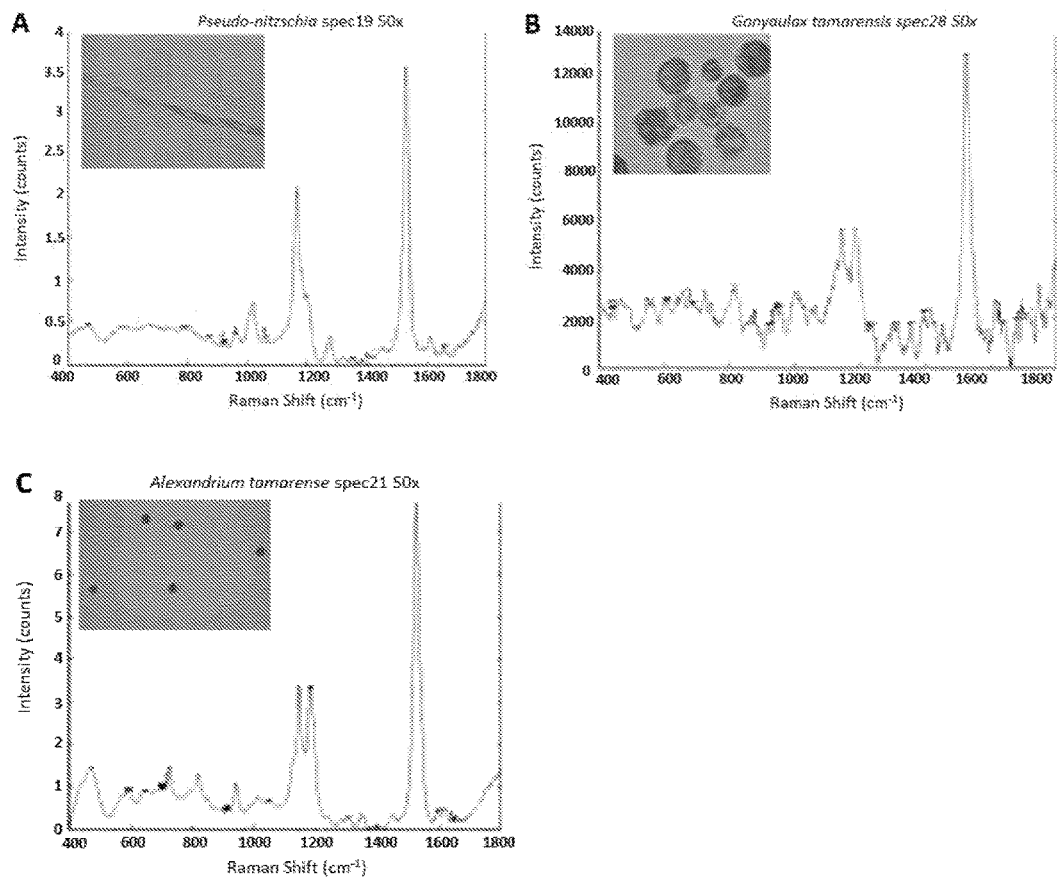
FIG. 5 depicts one embodiment of Raman spectra for single cells of (A) *Pseudo-nitzchia*, (B) *Gonyaulux tamarensis*, (C) *Alexandrium tamarense*. Panel D shows a composite showing the different responses of *Gambierdiscus* produced by lasers of different wavelengths (473 nm, 532 nm, 633 nm).

The optical splitter 27, which may be a dichroic filter and beam splitter, is arranged behind the lens 16 within the optical system 10 to allow the laser 15 excitation light to enter the optical path and be projected at the target 22 providing a defined region of Raman excitation (shown in FIGS. 4 and 5 by the white dotted line) on the order of about 50 µm in diameter. The optical splitter 27 then allows all of the reflected light (Raleigh plus Raman and Stokes scattering) to be directed back from the lens 16 and into the spectrometer 14 when the Raman scattered light is separated from the bulk of the reflected light. The raw Raman spectrum is then saved along with the ROI of the target 22.

The spectrometer 14 may be any suitable machine which may be integrated into the housing 12 and adapted to provide a spectrograph with the resolution to accurately classify the target's 22 species. In some embodiments, the spectrometer 14 is a micro Raman spectrometer 14 such as those commercially available from Kaiser Optical Systems, Inc. Wavelength calibration is performed using a neon light source, and the spectrometer 14 is calibrated regularly (e.g., hourly, daily, weekly) using a 520 $cm^{-1}$ peak of a polished silicon wafer.

Although any excitation source compatible with the spectrometer 14 may be used, the laser 15 is often selected to operate at a wavelength range of 300 nm to 700 nm, preferably, 400 nm to 600 nm, more preferably 500 nm to 600 nm, and specifically about 532 nm in some embodiments. In other embodiments, the laser 15 provides light of a wavelength approximately 473 nm, 532 nm, 633 nm, 785 nm, and/or 1064 nm although longer or shorter wavelengths may be used as deemed suitable by one skilled in the art. The laser 15 is focused using an objective (e.g., 10×, 20×, 30×, 40×, 50× magnification) at approximately 1-10 mW.

A single spectrum is obtained from a plurality of accumulations (e.g., 1, 2, 4, 6, 8, 10, 20, or more) and the exposure times are adjusted on the basis of the fluorescence in the target 22 to avoid saturation of the camera 11.

In one embodiment, a water-dipping Raman probe for external analysis of fluids is used to acquire spectra on admixtures of water comprising plankton directly from the environment. In this case, the Raman probe is placed up against the container holding the fluid sample or is dipped directly into the sample. The spectrometer 14 then creates a spectrograph of the sample for analysis and species determination.

The housing 12 fits or otherwise securely mounts the optical system 10 within the internal space of the housing 12; the housing 12 is also connected to the light source 17 via the connection means 19. The housing 12 is made from any suitable material adapted for an aquatic environment and resistant to degradation from external forces such as water, salt, bio-fouling, dust, and other environmental and circumstantial conditions. The housing 12 is preferably designed to withstand the pressure forces exerted by the surrounding environment which may vary depending upon the depth of desired deployment of the inventive device. In some embodiments, the housing 12 is comprised of aluminum or aluminum alloy. In other embodiments, the housing 12 is comprised of steel, stainless steel, steel alloy, or any suitable material adapted for an aquatic environment.

The components of the optical system 10 are generally secured by attachment members such as brackets, rings, supports, screws, nuts, bolts, pins, or the like to securely fasten and prevent undesired movement of the components even in rough environmental conditions or when the particle imaging device is in motion (e.g., towed, when in deployment, in transit). The attachment members may, in some cases, be adjustable to properly position the optical system 10 within the housing 12. In addition, the attachment members may allow for the precise adjustment of the optical components made by means such as fine adjustment screws or similar fasteners. Those skilled in the art will appreciate that many modifications and changes can be made to securely mount each component of the optical system 10 in a functional manner within the housing 12.

Target Imaging Space

As shown in FIG. 6, the target space 18 is defined by a region in the space disposed between the light source 17 and the optical system 10 (e.g., the path length) where the primary light beams 20 may intersect or converge. At the target space 18, a target 22, impinged by the converging primary light beams 20, will reflect, deflect, or refract the light to produce secondary light beams 21 which then impinge the distal face of the lens 16.

In general, the HAB detection system employs an open, free-flow space, referred to as the target space 18, wherein targets 22 present in the surrounding environment typically may move through the free-flow space without deterrence and without force (e.g., pumping). Free-moving organisms and particles may flow into the target imaging space 18, be imaged by the device and associated optical system 10, and continue to pass through as dictated by the natural flows of the surrounding environment such as the water current or even by the self-propelled movement of the target 22.

In many embodiments, the targets 22 move through the target space 18 without additional force (i.e., without external assistance). By allowing the plankton to enter the target space 18 without use of a pumping mechanism, a more accurate perspective of the population is obtained. Additionally, forced water movement may damage certain organisms with highly fragile features or disrupt the natural predator-prey interactions. As the inventive device may be utilized in deeper depths, use of a pump would also become problematic; in such case, the free-flow system provides a simple, reliable method of imaging the plankton community.

The focal volume may be modified based on the specific lens 16 and lighting source 17 specifications and arrangement. In some embodiments, the target space 18 (e.g., focal volume) is at least or about 1 cm³. In other embodiments, the target space 18 may be larger such as near 1 m³. In other embodiments, the target space 18 may be between 1 mm³ up to 5 m³ or more.

Data Communication

The HAB detection device often comprises a means to communicate the collected images and data to a local or remote location (e.g., vessel, vehicle, observatory node, buoy, mooring, off-shore platform, land-based facility, server, website, etc.) via an Ethernet interface. The preferred method of data communication is selected to be high-speed Ethernet (e.g., megabit, gigabit) wherein the images and data processed by the image processor (or raw data) is transmitted through a data network connection to one or more local or a remote locations as dictated by the user. The data generated by the continuous particle imaging device may be transformed into any suitable form or size for the transmission of the data to another location or a form or size compatible for a computer system.

In some embodiments, the capacity of the Ethernet connection is at least 1-megabit per second, up to 1-gigabit per second, 2-gigabits per second to 10-gigabits per second, 10-gigabits per second to 25-gigabits per second, or greater. Although an Ethernet connection is preferred, any suitable data connection capable of transmitting the digital images and data from the particle imaging device to another location may be employed with the present invention. In one embodiment, the digital images and data collected by the continuous particle imaging device are relayed to another location in real time via a data connection (e.g., Ethernet connection). In further embodiments, the images and data are transferred continuously. In other embodiments, transmission of the collected images/data is programmed to transmit periodically as defined by the user.

Image Processing and Classification

Imaging data (e.g., the digital image and data) is transmitted to the host computer such as the HAB detection device's computer in various embodiments and either stored directly onto a storage device or directed to a processing pipeline to conduct Bayer color decoding, color correction, light field normalization, extraction of the "Region of Interest" ("ROI") surrounding in-focus targets 22, and/or other requirement image processing procedures. In one embodiment, software running on the host computer will check each image to see if there are targets in the image which satisfy a series of criteria, including but not limited to, the number of contiguous pixels that are greater than a specified value using a defined blob detection routine, brightness threshold, and in-focus threshold. If any imaged target 22 meets the threshold criterion, the code places a bounding box around the blob (i.e., the imaged target) with an expansion factor of a user-controlled value in the configuration file. It will then write pixels of the ROI to a specified location on a local or remote storage device (e.g., hard drive). All of the pixels constituting each ROI are saved, thereby producing a full resolution of the image and eliminating the need to compress information.

The image processing procedure can also have several configurations. Optional configurations include, by way of example, ROI extraction and target classifications. Internal ROI extraction greatly reduces the bandwidth of information transmitted by the instrument to a remote or local storage location. In one embodiment, a custom Field Programmable Gate Array ("FPGA") coupled with a Graphical Processing Unit (GPU) and RISC-based ARM processor conducts all of the steps described above for on-instrument ROI extraction and target classification reducing the information stored by a factor of 10,000 or more.

Target classification has long been a challenge in the field as species recognition is often complicated by the variation within a species, and a good classifier must have enough flexibility to accommodate this intra-species variation while still able to distinguish between species. As it is far too time-consuming (and often inaccurate) to identify each image manually (e.g., by eye), [an automated classification system may be employed.] In many cases, the accuracy of species identification depends on the quality of the training sets of identified and classified species used for comparison with the imaged targets, including species-related features, size, profile, orientation, color, color distribution, and such.

Classification may also be performed on a remote computer, operating on ROIs that have been transmitted through such as an Ethernet connection or other transmission conduit or device. Primarily, ROI extractions are performed on-board. Classifications and subsets of images can be transmitted across low bandwidth ports, and the open board classifier and configuration files may also be updated across this link.

Target classification is often divided into categories which may vary depending up the plankton communities present in the sampling environment. These categories may be based on any specific characteristics of the plankton and may include classification on the domain, kingdom, phylum, class, order, family, genus, or species level. In another embodiment, target classification is divided into 11 primary categories representing the main plankton taxonomic groups present in the sampling area: filamentous cyanobacteria (*Trichodesmium* spp.), diatoms, radiolarians (primarily acantharians), foraminiferans, copepods, isopods, cnidarians, other zooplankton (e.g., appendicularians, ostracods, and larval molluscs), mysids, and fish; and a marine snow "particle" category regrouping all non-living particles. The size range of this particular set of particles is approximately 100 m to 10 mm in length. Any specific training set of plankton ROIs may be delivered to the continuous particle imaging device, allowing the device to be highly adaptable and provide accurate classification of desired plankton and particles. Each training set may be focused on a specific size scale, a select level in the taxonomic hierarchy (e.g., species, genus, family, order, etc.), a select distinguishing feature (e.g., profile, color, transparency, etc.), or any suitable criteria desired by the user to facilitate classification of the imaged targets. Additionally, each training comprises at least one category of at least one microorganism or particle up to 5, 10, 20, 30, 50, 100, or even up to 1,000 unique microorganism identifications (IDs) and/or categories or more.

While the present device employs light microscopy as part of the classification process, the HAB detection device uses the Raman spectroscopic assembly 13 to produce a unique fingerprint in the form of a Raman spectrum to further accurately detect and quantify toxic species. FIG. 3 depicts one example of a Raman spectroscopic signature comprising peaks for a common algal bloom toxin saxitoxin. The method of sampling and evaluation by the HAB detection system provides a method of whole cell, non-contact analysis which can detect not only the presence of plankton comprising the algal toxins but also more accurately determine a concentration at which the toxin is currently present in the environment.

In some embodiments, quantification (e.g., counts, population) and/or size measurements are determined automatically by the present invention. In another embodiment, information collected on the imaged targets is presented as a time series of target data and is either transmitted to another platform or location (e.g., automatically, in real-time) or stored on the storage device for later retrieval.

The accuracy of the classification can be adjusted by focusing on certain critical points. First, accuracy can be adjusted by the number of high quality training sets. As more extensive training sets are produced, the classifier may be run over all of the ROIs that have been collected for a particular time period. Second, by combining certain feature extraction techniques, the accuracy can be increased exponentially. In the preferred embodiment, Gabor wavelets are used to extract information on the texture, morphology, and orientation of the target 22. Then, the color angles 25 are used to get information on the color intensity in hue space and color distribution throughout a target. The combination of these two feature sets in the preferred embodiment is extremely powerful. Third, the classifier device itself can be calibrated. The use of a Support Vector Machine is disclosed, but the Random Forests classification method in parallel are also implemented. The output from the Gabor filters and color angles 25 results more than 1000 features. The dimensionality of this set can be reduced by principle component analysis before training and classification.

The "focus" parameter operates by subtracting a decimated and smoothed, or blurred, image from the original image. The closer the resultant image is to the original, the less in-focus the original. The focus threshold also partially defines the image volume and is critical to the calibration of the instrument.

In its most basic form, as the ROIs come in from the camera 11 and telecentric lens 16 module, an algorithm is used to compute a series of feature extractions with the image processor and a statistical machine vision classifier (e.g., Support Vector Machine, Random Forests, Boosted Regression Trees), is run to classify the ROI into one of many categories that have been manually set up and trained on by the user to produce a data output.

In addition to the imaging processing components described above, embodiments of the HAB detection system often include a digital data storage device for storing the collected images and/or data. Such devices are capable of reliable image collection and/or data transfer without degradation to performance or data quality even when the particle imaging system is disposed in an aquatic environment with rough environmental conditions. The electronics and software are generally disposed in the housing 12. The storage device may be configured for flexibility of use in terms of data storage capacity and data transfer capabilities depending on the specific use of the particle imaging system. In some embodiments, the storage device collects the images and data obtained by the optical assembly and archives them for later retrieval in either a raw or processed format. In other embodiments, the storage device is capable of storing the images and data and relaying the collected information (automatically or on command) to a selected location such as the attached mooring, a vessel, a land-based facility, or other desired platform. The storage device may include one or more hard drives as necessary for the length of the deployment of the system. In further embodiments, the storage device transfers the collected data in real time (e.g., immediately, after imaging, after image processing, continuously). In other embodiments, the storage device periodically sends the collected images and data as dictated by the user's settings. In some embodiments, the storage device is configured for high-speed recording/processing (e.g., data reading, writing, retrieving, caching) of data including rates of at least 10 megabit/s, at least 100 megabit/s, at least 200 megabit/s, at least 400 megabit/s, at least 500 megabit/s, up to 1 gigabit/s, up to 2 gigabit/s, up to 5 gigabit/s, or greater.

Should it be desired to have the collected images and data relayed immediately to a selected platform, the storage device may comprise an established communication connection such as by an Ethernet interface. In some embodiments, the storage device is coupled to an Ethernet connection via a copper cable or a fiber optic cable such as a CAT5, a CAT5e, a CAT6 cable, or other suitable connection means of data communication. Certainly, other alternative methods of relaying the collected images and data may be equally employed with the present invention.

As a cabled instrument in its most basic configuration, the power supply (e.g., batteries or the like) and Ethernet are supplied from an external source including, but not limited to, a towed vehicle, CTD rosette, or cabled observatory or mooring. The system can be controlled from ship or shore through custom software and a configuration file that contains the operating information. In the preferred embodiment, the image data is transmitted as raw 12 bit Bayer encoded 6 megapixel images to the host computer.

Additionally information on image processing and target classification which may be utilized with the present methods may be provided in U.S. Pat. No. 7,415,136 incorporated by reference in entirety.

The HAB detection device is capable of multiple configurations and magnifications. The specific configuration or magnification will depend upon the imaging task at hand, with the invention providing solutions for a wide array of applications including being towed or moored. The system will also provide for vehicle operations that will image marine snow, zooplankton, phytoplankton, and a variety of microplankton. The HAB detection device may be affixed, attached, mounted, positioned, or otherwise secured to a vehicle or platform. In some embodiments, the particle imaging system is attached to a vehicle such as an autonomous underwater vehicle (AUV), a remotely operated vehicle (ROV), a glider (e.g., Jet Yak), an autonomous profiling mooring (e.g., profiler), a submarine, a mini submarine, a human operated vehicle (HOV), a towed body, or any vehicle deemed suitable for underwater operations. In other embodiments, the particle imaging system is attached to a platform, moored, or otherwise affixed to remain stationary such as a mooring, a buoy, a float, an off-shore station, a profiler which remains stationary for a period of time at selected depths, or the like.

The present system may also be towed behind a marine boat or watercraft wherein the HAB detection device is tethered or suitably connected to the watercraft by any means known in the art. Additionally, the present invention may be designed to operate out of the water on a platform such as a counter or a lab bench.

Example 1

This example further describes plankton species and Raman peaks associated with specific compounds present within the algal cells used for the detection and analysis of HABs in the environment.

Figure 8:
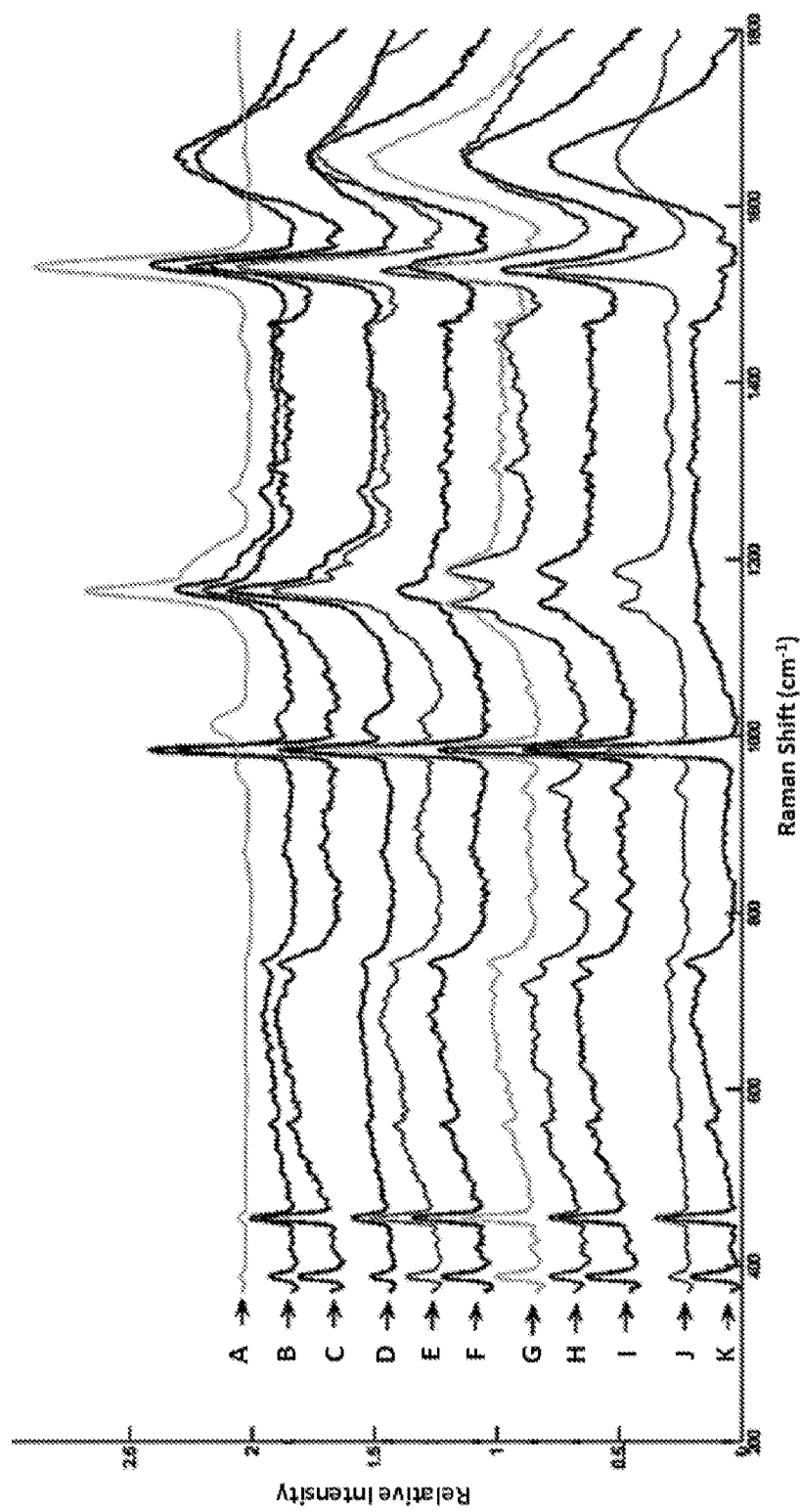
FIG. 8 depicts a spectra of a variety of peaks common to all species and some that are specific to certain groups. The species are labeled as such: (A) *Isochrysis aff. galbana* (TISO); (B) *Chaetoceros* sp.; (C) *Karenia brevis*; (D) *Chattonella subsalsa*; (E) *Chattonella marina*; (F) *Alexandrium tamarense*; (G) *Gambierdiscus belizeanus*; (H) *Alexandrium fundyense*; (I) *Heterocapsa*; (K) *Gymnodinium catenatum*.
Figure 9:
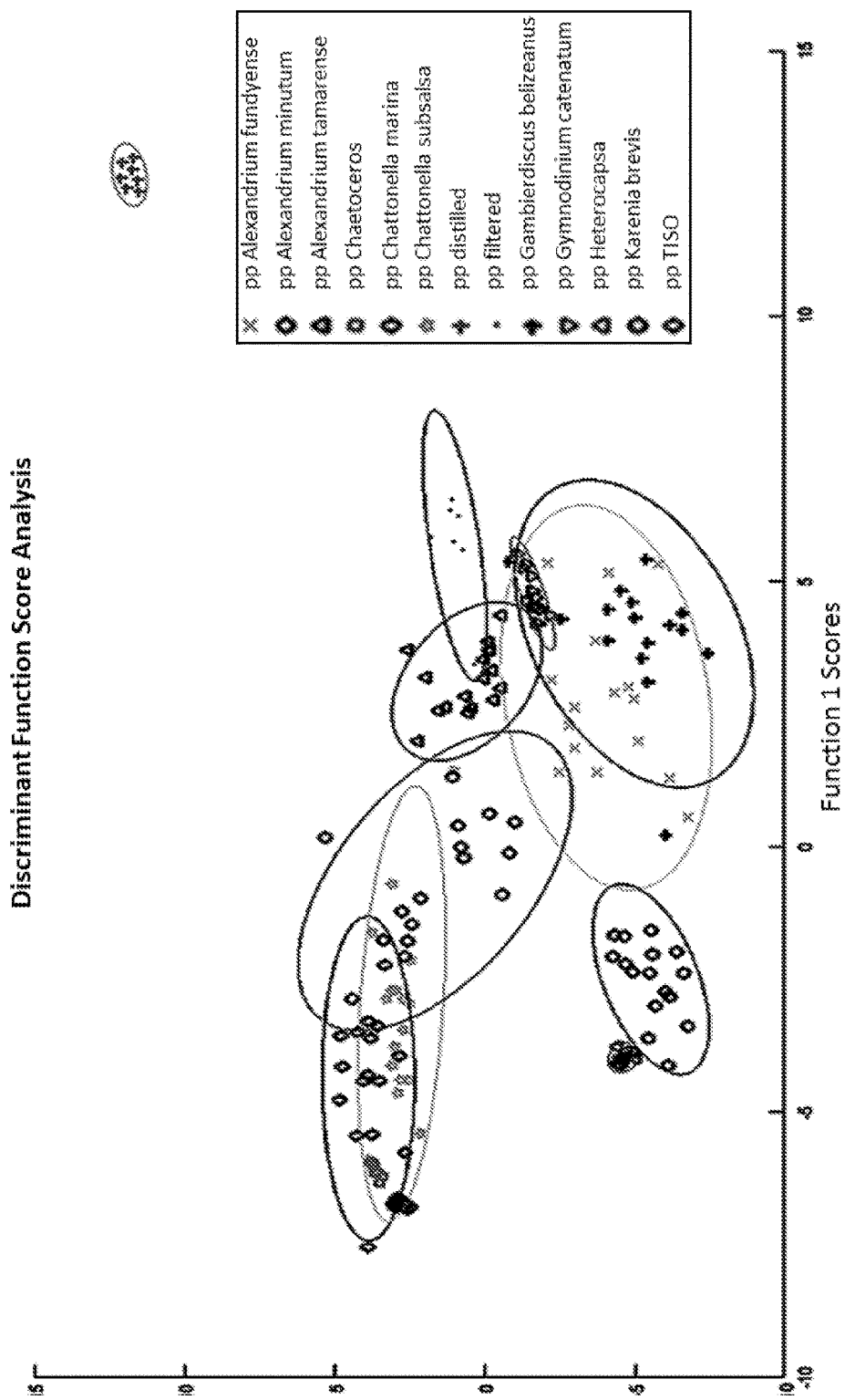
FIG. 9 depicts a Leave-One-Out Cross Validation (LOOCV) allowed assembly of a confusion matrix showing the relative classification accuracies for each sample.
Figure 11:
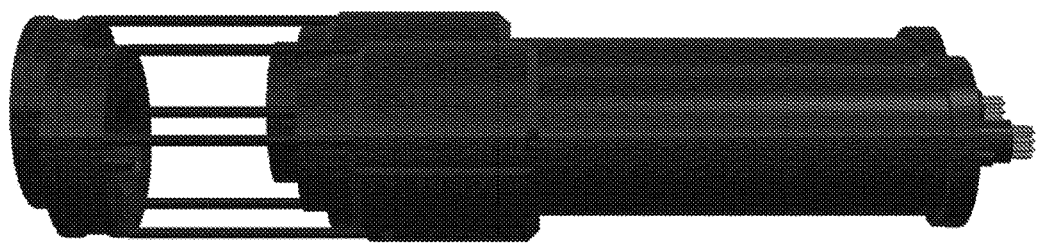
FIG. 11 illustrates one illustrated embodiment of the device.

The strains listed in Table 1 were obtained from the National Center for Marine Algae and Microbiota (NCMA), subcultured in L1 media and analyzed using a bulk Raman probe at 532 nm. The processed (background corrected) spectra of 15 repeated analyses (FIG. 8) indicated a variety of peaks common to all species and some that are specific to certain groups (e.g., single peak at 1120 cm$^{-1}$ versus dual peaks at 1165 cm$^{-1}$ and 1187 cm$^{-1}$). Most of the peaks can be attributed to pigments (Chlorophyll a, b, c [915, 1495, 1165, 1187 cm$^{-1}$], β-Carotene [1008, 1157, 1265, 1525 cm$^{-1}$]) and fatty acids and lipids. Peaks associated with saxitoxin (e.g., 533, 800, 950, 1185, 1238, 1324, 1491, 1548, 1611 cm$^{-1}$) are present in some species and not in others as expected. PCA on replicate spectra was performed followed by LDA using each known spectra as ground truth to train the classifier. A Leave-One-Out Cross Validation (LOOCV) allowed assembly of a confusion matrix showing the relative classification accuracies for each sample. Accuracies ranged between 62% and 100% with a mean of 88%. Lowest discrimination accuracies were between *Alexandrium fundyense* and *Gambierdiscus belizeanus*, which are never found together in the field. *Alexandrium fundyense* and *A. tamarense* do ecologically overlap, and were 100% separable. These results provide confidence that many species can be discriminated using their Raman signatures alone.

TABLE 1

Species and strains of HABs analyzed (National Center for Marine Algae and Microbiota (NCMA) Culture Collection of Marine Phytoplankton (CCMP) culture designation and collection location).

| Genus Species | CCMP | Collection Location |
|---|---|---|
| *Alexandrium minutum* | 113 | Ria de Vigo, Spain |
| *Alexandrium tamarense* | 1598 | Hong Kong, China |
| *Alexandrium fundyense* | 1911 | Sequim Bay, WA |
| *Chattonella subsalsa* | 217 | Caribbean |
| *Chattonella marina* | 2050 | Seto Inland Sea, Japan |
| *Karenia mikimotoi* | 429 | Sutton Harbor, England |
| *Gambierdiscus belizeanus* | 401 | St. Barthelemy Island, Caribbean |
| *Gymnodinium catenatum* | 1937 | Ria de Vigo, Spain |
| *Karenia brevis* | 2229 | Manasota Key, Florida |

Libraries are established of Raman spectroscopic fingerprints and as many of the peaks identified through the literature or by a theoretical understanding of Raman signals from different carbon bonds and hydroxyl group (—OH) stretching. Standard classification techniques such as principal component analysis (PCA) with linear discriminant analysis are used to group similar peak locations relative to known standards. Random Forest classifiers provide assistance in sorting and classifying spectra directly without completing a PCA analysis first. Additionally, spectra of several synthesized neurotoxins and several analogs of saxitoxin are used to gather spectra to enhance the library.

As shown in FIG. 8, a series of MRS runs were conducted using the 532 nm laser on the toxic dinoflagellate *Gambierdiscus silvae* obtained from a coral reef off of St. Thomas. Shown in FIGS. 4A and 4B, the MRS spectra from two different cells using a 50× objective and a small exposure site (2 μm—note the dotted line defining exposure site on each cell in FIGS. 4A and 4B). The spectra are nearly identical. Major peaks are located at 1012 $cm^{-1}$ and 1159 $cm^{-1}$ (beta-carotene), 1185 $cm^{-1}$ and 1304 $cm^{-1}$ (chlorophyll), and 1452 $cm^{-1}$ and 1525 $cm^{-1}$ (beta-carotene). Similar spectra were recorded at 25× and 10× showing that the signature produced by the dinoflagellate is distinct and independent of magnification (FIGS. 4C and 4D).

Cells of the toxic diatom *Pseudo-nitzchia* were targeted possibly containing domoic acid (FIG. 5A), *Gonyaulux tamarensis* (FIG. 5B), and *Alexandrium tamarense* containing PSP (FIG. 5C). The two dinoflagellates produced spectra similar to *Gambierdiscus* with the same pronounced peaks for beta-carotene and chlorophyll, with the exception that *G. tamarensis* showed many more bands between 600 $cm^{-1}$ and 1000 $cm^{-1}$. Conversely, *Pseudo-nitzchia* lacked the double peaked bands at 1012 $cm^{-1}$ and 1159 $cm^{-1}$ (b-carotene). Other distinctiveness could be discerned. Shown in FIG. 5D is a composite showing the different responses of *Gambierdiscus* produced by lasers of different wavelengths (473 nm, 532 nm, 633 nm). Unexpectedly, the longest wavelength (633 nm) produced the broadest signal and highest level of fluorescence. There was very little differentiation of bands at this wavelength compared to the lower frequencies. Both green and blue lasers produced a rich set of bands.

Example 2

This example provides Table 2 showing a representative example of harmful algal bloom targets of interest which may be detected by the present invention and their associated toxin.

| Group | Class | Species |
|---|---|---|
| Species of HAB that are non-toxic but cause anoxic conditions | Dinoflagellates | *Noctiluca scintillans*, *Akashiwo sanguinea*, *Gonyaulax polygramma*, *Scrippsiella trochoidea* |
| | Cyanobacteria | *Trichodesmium erythraeum*, *Aureococcus anophagefferens* |
| Species that are non-toxic to humans but harmful to fish | Dinoflagellates | *Cochlodinium polykrikoides*, *Karenia mikimotoi*, *Karenia brevisulcata* |
| | Haptophytes | *Prymnesium polylepis*, *Prymnesium parvum* |
| | Raphidophytes | *Heterosigma akashiwo*, *Chattonella antiqua*, *Chattonella marina* |
| Species that produce and release very potent toxins | Dinoflagellates | *Alexandrium fundyense*, *Alexandrium minutum*, *Gymnodinium catenatum*, *Pyrodinium bahamense*, *Alexandrium catenella*, *Alexandrium Tamarense*, *Azadinium spinosum*, *Gambierdiscus polynesiensis*, *Dinophysis acuta*, *Dinophysis acuminata*, *Dinophysis fortii*, *Dinophysis norvegica*, *Dinophysis sacculus*, *Prorocentrum lima*, *Karenia brevis* |
| | Diatoms | *Pseudo-nitzschia australis*, *Pseudo-nitzschia multiseries*, *Pseudo-nitzschia seriata* |
| | Cyanobacteria | *Anabaena circinalis*, *Cylindrospermopsis raciborskii*, *Microcystis aeruginosa*, *Planktothrix rubescens*, *Nodularia spumigena* |

| Class | Species | Toxin |
|---|---|---|
| Dinoflagellates | *Azadinium spinosum* | Azaspiracid Shellfish Poisoning (AZP) |
| Dinoflagellates | *Gambierdiscus polynesiensis* | Ciguatera Fish Poisoning (CFP) |
| Dinoflagellates | *Dinophysis acuta, Dinophysis acuminata, Dinophysis fortii, Dinophysis norvegica, Dinophysis sacculus, Prorocentrum lima* | Diarrhetic Shellfish Poisoning (DSP) |
| Dinoflagellates | *Karenia brevis* | Neurotoxic Shellfish Poisoning (NSP) |
| Dinoflagellates | *Alexandrium fundyense, Alexandrium minutum, Gymnodinium catenatum, Pyrodinium bahamense Alexandrium catenella, Alexandrium tamarense* | Paralytic Shellfish Poisoning (PSP) |
| Diatoms | *Pseudo-nitzschia australis, Pseudo-nitzschia multiseries, Pseudo-nitzschia seriata* | Amnesic Shellfish Poisoning (ASP) |
| Cyanobacteria | *Anabaena circinalis, Cylindrospermopsis raciborskii, Microcystis aeruginosa, Planktothrix rubescens, Nodularia spumigena* | Cyanobacterial Toxin Poisoning (CTP) |

Example 3

In other embodiments, the present invention may be used to image, observe, classify, and/or otherwise detect microplastics in the surrounding environment as targets of interest.

As plastic debris is accumulating in the aquatic environment, it is becoming a highly important topic for both short-term and long-term repercussions. Currently, no autonomous vehicles or sampling devices exist for quantifying and characterizing the millimeter size and smaller marine debris. Furthermore, no submersible Raman spectroscopy-based sensors or light microscopes currently exist for such applications.

An estimated 299 million metric tons of plastic were used globally in 2013. A great deal of debris from this usage eventually makes its way to the ocean. The effects of Plastic Marine Debris (PMD) are a potential threat to marine biota, since even the earliest scientific reports pointed to a multitude of potential interactions with microbes, fish, and zooplankton (Carpenter et al (1972) Polystyrene Spherules in Coastal Waters. Science 178 (4062)). PMD has now been found to have permeated the most distant parts of the sea, from remote mangroves, to deep sea canyons, and areas of *Antarctica*. In the Danube River in Germany, for example PMD particles have been found to outnumber fish larvae and contribute an estimated 4.2 metric tons of plastic per day into the Black Sea (Lechner et al. (2014) The Danube so colorful: A potpourri of plastic litter outnumbers fish larvae in Europe's second largest river. Environmental Pollution. 188: 177-181).

A significant amount of the plastic believed to enter the ocean remains unaccounted for, even though PMD carried on major ocean currents and transported to central gyres may persist there for decades. Calculations have indicated as much as 12.7 million metric tons of plastic makes its way to the sea annually. Nevertheless, even the most recent ocean surveys have not accounted for several orders of magnitude of plastic believed to have entered the marine environment. Furthermore, the data that is available derives from analyses performed only at near surface depths, and the distribution of deeper subsurface plastics requires attention to more fully understand PMD distribution in the ocean environments. Therefore, there is a great need to determine distribution of plastics in the water column and sediments of one of the earth's greatest aggregations of plastic marine debris which will further establish the foundational data to inform remediation activities on ocean life ecosystems and transport processes.

The described features, advantages, and characteristics may be combined in any suitable manner in one or more embodiments. One skilled in the relevant art will recognize that the circuit may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment.

What is claimed:

1. A portable detection device for detecting and quantifying a target of interest while in an aquatic environment, comprising:
   a high-resolution optical system comprising a Raman spectroscopic assembly, disposed in a housing;
   a lens with an image face and a defined focal length;
   a target space, capable of at least temporarily accommodating at least one target to be detected, wherein the target space is configured in the device for free flow so as to allow said at least one target to enter and exit from any side of the target space; and
   a power source, operably connected to said optical system;
   wherein the Raman spectroscopic assembly receives light information from a target to provide a spectrum associated with the target, said spectrum is analyzed for defined Raman peaks, and the device is capable of operating in an aquatic environment.

2. The device of claim 1 further comprising a light source, disposed distal to the image face capable of producing two or more primary light beams which do not intersect with the image face of the lens wherein said primary beams interact with a target in the target space to produce a secondary light beam which impinges on the distal face of the lens.

3. The device of claim 2 further comprising a connection means connecting said light source to the housing of the optical system at a distance away from said optical system.

4. The device of claim 1, wherein the optical system further comprises a darkfield optical assembly adapted for imaging the target.

5. The device of claim 1, wherein the Raman spectroscopic assembly comprises a spectrometer, an optical splitter, and a laser adapted to impinge the target.

6. The device of claim 1, wherein the lens is an infinity corrected lens.

7. The device of claim 2, wherein the light source comprises one or more light-emitting sources capable of emanating primary light beams onto a target.

8. The device of claim 7, wherein each light-emitting source emanates light selected from the group comprising monochromatic light, polychromatic light, white light, red light, ultraviolet light, and a combination thereof.

9. The device of claim 2, wherein the light source is capable of intermittent illumination at a specified rate relative to the camera's exposure duration.

10. The device of claim 2, wherein the light source is disposed a distance of under 6 cm from the optical system.

11. The device of claim 1, wherein the device is capable of submergence in an aquatic environment and may be adapted to image targets at depths between 0.5 m, 1 m, 5 m, 10 m, 20 m, 30 m, 50 m, 100 m, 250 m, 500 m, 1,000 m, 2,000 m, and 6,000 m.

12. The device of claim 2 further comprising an anti-fouling system selected from said light source further comprising one or more ultraviolet light-emitting sources, a lens with anti-fouling properties adapted to pass undistorted image information through said lens, a mechanical defouling device, or a combination thereof.

13. The device of claim 12, wherein the anti-fouling system provides an anti-fouling capacity selected from emitting ultraviolet light intermittently offset in time from the illumination for capturing images, emitting an ultraviolet light dose for a pre-determined length of time, or a combination thereof.

14. The device of claim 12, wherein the anti-fouling system comprises a lens with anti-fouling properties such as a coating of colloidal titanium dioxide nanoparticles.

15. The device of claim 1, wherein the device is disposed in an aquatic environment and disposed from a platform selected from the group comprising an autonomous underwater vehicle (AUV), a remotely operated vehicle (ROV), a glider, a profiler, a submarine, a mini submarine, a human operated vehicle (HOV), a mooring, a buoy, a float, an off-shore station, a watercraft for towing said device, and a counter.

16. The device of claim 1, wherein the target is one or more targets selected from the group comprising plankton, dinophagellates, cyanobacteria, haptophytes, raphidophytes, diatoms, particles, microplastics, and a plankton comprising a compound of interest.

17. The device of claim 1 further comprising a telemetry means of communicating information on the spectrum to an external source, and wherein said spectrum is analyzed for defined Raman peaks via a comparison to a library of spectra for classification of the target.

18. A method of detecting the presence of a target, the steps comprising:
providing a device comprising an optical system with a lens and a Raman spectroscopic assembly, wherein the device is capable of operating in an aquatic environment;
allowing at least one target to enter an open, free flow target space to be detected by the optical system, wherein said at least one target is allowed to enter and exit from any side of said target space;
employing the Raman spectroscopic assembly to impinge the target with a laser; and
collecting the light information of the impinged target with the lens and directing the Raman scattered light to the spectrometer to produce a spectrum associated with the target.

19. The method of claim 18, wherein the spectrum is analyzed for defined Raman peaks via a comparison to a library of spectra for classification of the target.

20. The method of claim 18, wherein the optical system further comprises a darkfield optical assembly, and the darkfield optical assembly is adapted to capture an image of the target offset in time from the acquisition of the spectrum.

21. The method of claim 20, wherein the image and the spectrum are each compared to a library of images and spectra of known targets for classification of the target.

22. The method of claim 18 further comprising the step of communicating the image and spectrum to a storage device disposed within said system.

23. The method of claim 18, wherein the image and spectrum are transmitted from the storage device to a location external to the device selected from a vessel, a vehicle, a land-based facility, a buoy, a mooring, a server, and a website.

24. The method of claim 18, wherein the target is one or more targets selected from the group comprising plankton, dinophagellates, cyanobacteria, haptophytes, raphidophytes, diatoms, particles, microplastics, and a plankton comprising a compound of interest.

25. The device of claim 2, wherein the Raman spectroscopic assembly comprises a spectrometer, an optical splitter, and a laser adapted to impinge the target.

* * * * *